United States Patent
Koch

(10) Patent No.: US 9,761,804 B2
(45) Date of Patent: Sep. 12, 2017

(54) OLIGOMERIC ORGANIC LIGHT EMITTING DIODE (OLED) MATERIALS CONTAINING MULTIPLE CROSSLINKING FUNCTIONS

(71) Applicant: LOMOX LIMITED, Abercynon (GB)

(72) Inventor: Gene Carl Koch, Bishop Auckland (GB)

(73) Assignee: Lomox Limited, Congleton, Cheshire (GB)

(*) Notice: Subject to any disclaimer, the term of this patent is extended or adjusted under 35 U.S.C. 154(b) by 165 days.

(21) Appl. No.: 14/399,296

(22) PCT Filed: May 9, 2013

(86) PCT No.: PCT/GB2013/000201
§ 371 (c)(1),
(2) Date: Nov. 6, 2014

(87) PCT Pub. No.: WO2013/167857
PCT Pub. Date: Nov. 14, 2013

(65) Prior Publication Data
US 2015/0097145 A1    Apr. 9, 2015

(30) Foreign Application Priority Data
May 9, 2012    (GB) .................................. 1208115.4

(51) Int. Cl.
| | |
|---|---|
| *H01L 51/00* | (2006.01) |
| *C07C 43/215* | (2006.01) |
| *C07C 69/52* | (2006.01) |
| *C09K 11/06* | (2006.01) |
| *H05B 33/14* | (2006.01) |
| *H01L 51/50* | (2006.01) |

(52) U.S. Cl.
CPC ........ *H01L 51/0039* (2013.01); *C07C 43/215* (2013.01); *C07C 69/52* (2013.01); *C09K 11/06* (2013.01); *H01L 51/005* (2013.01); *H05B 33/14* (2013.01); *C09K 2211/1416* (2013.01); *C09K 2211/1425* (2013.01); *C09K 2211/1433* (2013.01); *C09K 2211/1458* (2013.01); *C09K 2211/1466* (2013.01); *C09K 2211/1483* (2013.01); *H01L 51/50* (2013.01); *H01L 51/5012* (2013.01); *H01L 51/5048* (2013.01)

(58) Field of Classification Search
None
See application file for complete search history.

(56) References Cited

U.S. PATENT DOCUMENTS

2011/0175069 A1    7/2011    Son et al.

FOREIGN PATENT DOCUMENTS

| EP | 2194582 A1 | 6/2010 |
|---|---|---|
| JP | 2003043713 A | 2/2003 |
| JP | 2005036223 A | 2/2005 |
| WO | WO-2013167863 | 11/2013 |

OTHER PUBLICATIONS

Hai-Lei Cui et al., "Dual Organocatalysis: Asymmetric Allylic-Allylic Alkylation of [alpha],[alpha]-Dicyanoalkenes and Morita-Baylis-Hillman Carbonates", Chemistry—A European Journal, vol. 15, No. 7, Feb. 2, 2009 (Feb. 2, 2009), pp. 1574-1577.

Alvaro et al., "Stereoselective synthesis of substituted 2,5-diazabicyclo[2.2.1]heptanes by iodine-mediated cylization of optically pure compounds containing the 4,5-diamino-1,7-octadiene and 1,2-diamino-4-alkene moieties", Tetrahedron, Elsevier Science Publishers, Amsterdam, NL, vol. 63, No. 50, Oct. 31, 2007 (Oct. 31, 2007), pp. 12446-12453.

Bassindale M J et al., "Employment of a cyclobutene ring-opening metathesis reaction towards a concise synthesis of (=/−)-sporochnol A", Tetrahedron Letters, Elsevier, Amsterdam, NL, vol. 42, No. 51, Dec. 17, 2001 (Dec. 17, 2001), pp. 9055-9057.

Contoret A. E. A. et al., "The Photopolymeriyation and Cross-linking of Electroluminescent Liquid Crystals Containing Methacrylate and Diene Photopolymerizable End Groups for Multilayer Organic Light-Emitting Diodes", Chemistry of Materials, American Chemical Society, Washington, US, vol. 14, No. 4, Mar. 20, 2002 (Mar. 20, 2002), pp. 1477-1487.

International Search Report on PCT/GB2013/000201, date of mailing Aug. 5, 2013.

*Primary Examiner* — Katie L Hammer
(74) *Attorney, Agent, or Firm* — Dority & Manning, P.A.

(57) ABSTRACT

OLED materials having the formula: T-A(-S-B(-P-B)m-S-A)n-T where A are independently selected rod-shaped, rigid molecular core units, S are independently selected flexible spacer units, B are polymerisable crosslinking groups independently selected, P are spacer groups independently selected, T are independently selected end groups, m are independently selected from values of from 1 to 4, n is equal to I to 3.

10 Claims, No Drawings

OLIGOMERIC ORGANIC LIGHT EMITTING DIODE (OLED) MATERIALS CONTAINING MULTIPLE CROSSLINKING FUNCTIONS

This application is a 35 U.S.C §371 national stage of International Application No. PCT/GB2013/000201, filed May 9, 2013, which claims priority of GB Patent Application No. 1208115.4, filed May 9, 2012. The entire contents of each of the aforementioned applications are incorporated herein by reference. OLED materials are known from U.S. Pat. No. 6,867,243 having the generic structure:

B-S-A-S-B where A is a rigid, rod or lathe-like molecular nucleus, S are flexible spacers, and B are crosslinking groups.

In these materials the central core (A), generally a highly conjugated aromatic ring system, confers the desired light emitting or charge transporting properties on the materials, and the crosslinking groups (B) allow the materials to be crosslinked, usually through exposure to UV radiation, into an insoluble, polymer matrix film. Thus, the materials can be solvent cast onto electronic substrates and photopatterned much as one would do with a photoresist.

The flexible spacers serve to mechanically and electronically insulate the molecular nuclei (A) from the crosslink connections into the polymer matrix formed through UV exposure. Without this isolation, energy of excitation produced in the molecular nuclei to, for instance, initiate light emission would be drained off into the polymer matrix destroying the desired optoelectronic effect. The spacers (B) are also necessary, in combination with the rod-like shape of the molecular nuclei, to promote liquid crystalline behaviour in the uncrosslinked materials. It has been found that liquid crystalline order is highly desirable in these materials, both to increase desirable properties such as carrier mobilities, and also to allow to the materials to be cast in highly ordered films with no disruptive defects such as the defects that occur in polycrystalline organic films.

It has further been found that it is highly desirable to incorporate one or more 9,9-disubstituted fluorene aromatic units into molecular nucleus (A). If the substituent(s) at the 9-position on the fluorene ring are sufficiently bulky, this substitution serves a threefold purpose. First, it increases the solvent solubilities of the materials so that they may be solvent processed. Second, this substitution promotes the thermodynamic stability of the nematic liquid crystalline phase over the crystalline or smectic phases that might also occur in these materials making it possible to cast films with nematic ordering. And third, this substitution provides sufficient separation between adjacent molecular nuclei to limit unwanted intermolecular mechanical and electronic interactions that would drain off energy of excitation.

Fluorene functional units that have been used in this respect are, for instance,

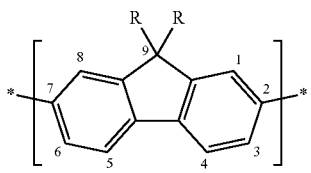

where R represents n-alkyl groups substituted at the 9 positions. (See U.S. Pat. No. 6,867,2430.) Further examples are spirocycloalkylfluorenes such as

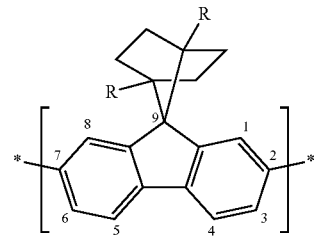

where R represents alkyl groups. (See WO2009087364.) In both these case substitution of the fluorene units into the molecular nucleus occurs at the 2 and 7 positions so as to maintain the nucleus' linear nature.

The materials described above have proven useful for use in OLEDs both as light emitters and as charge transporting materials. An important aspect of their application is their film forming properties since they can only be formed into useful structures if they can be applied to a surface in a uniform layer. Since the material layers in OLED devices are in general quite thin, these materials must be applied by spin coating, ink jet printing, or coating from a slot die in quite dilute solution. The low viscosity of these materials in dilute solution makes it difficult to form uniform films using the above techniques.

An approach to increasing the viscosity of solutions of the B-S-A-S-B materials is to increase the length of the molecular cores of the materials. Molecular cores (A) have been produced containing up to five fluorene units yielding molecules having molecular weights in excess of 2000. While these molecules do have better film forming properties and also give superior light emission efficacies, they are expensive to produce and are best suited as dopants in a polymer matrix formed from lower cost materials.

The present invention provides liquid crystalline, photopolymerisable host materials having suitable electronic properties, but which are relatively inexpensive to make The invention, in one aspect, comprises materials having the formula:

T-A(-S-B(-P-B)$_m$-S-A)$_n$-T where
A are independently selected rod-shaped, rigid molecular core units,
S are independently selected flexible spacer units,
B are polymerisable crosslinking groups independently selected,
P are spacer groups independently selected,
T are independently selected end groups,
m are independently selected from values of from 1 to 4,
n is equal to 1 to 3.

The crosslinking groups may be chosen so as to allow the molecules to be polymerised into a polymer matrix, particularly by exposure to UV. The molecular nucleus or core units and also the spacer units may be chosen such that the material displays liquid crystalline order and most preferably that it displays nematic order. It is also preferred that the core units are chosen so as to promote either light emitting or charge transporting properties, or both, in the product polymer matrix.

The rod-shaped, rigid molecular core units (A) may be any conjugated aromatic ring systems, but it is preferred that they have the general structure:

-E-F-(E-F)$_n$-E- wherein E may be independently chosen from a single bond or an aromatic diradical disubstituted so as to maintain the linear nature of rigid molecular core A, and wherein F is a diradical containing a fluorene, azafluorene or polyazafluorene aromatic ring system and which is disubstituted so as to maintain the linear nature of the rigid molecular core A, and wherein n is between 0 and 7, preferably between 0 and 4.

Examples of E sub-units are:

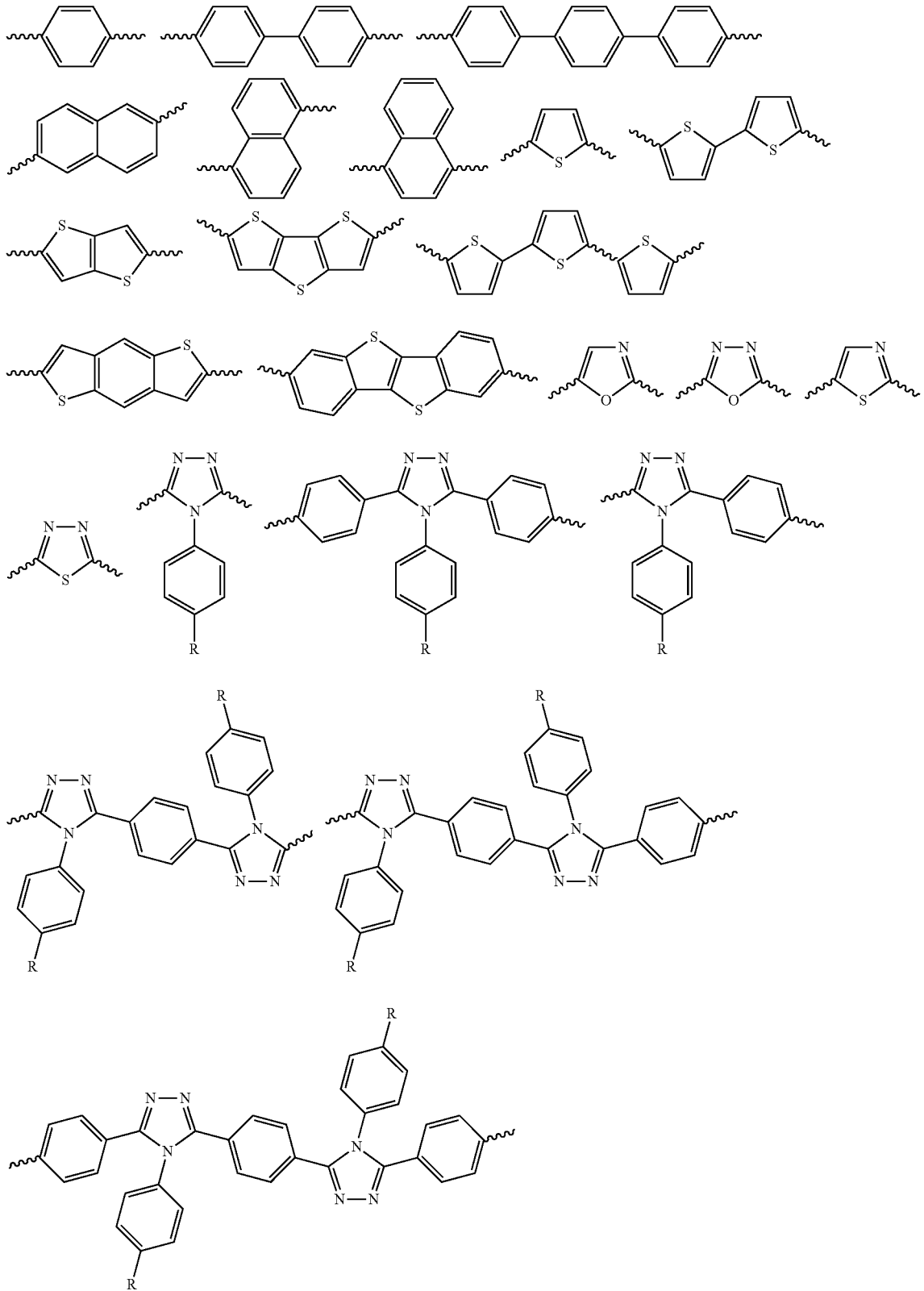

-continued
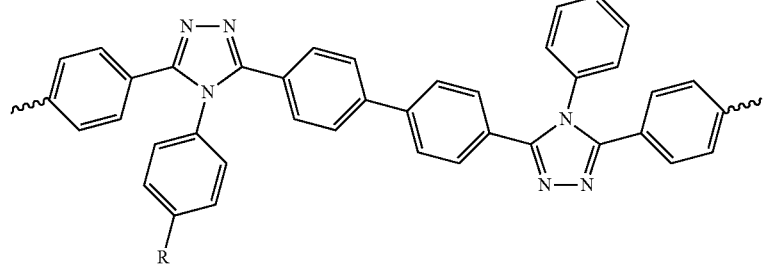
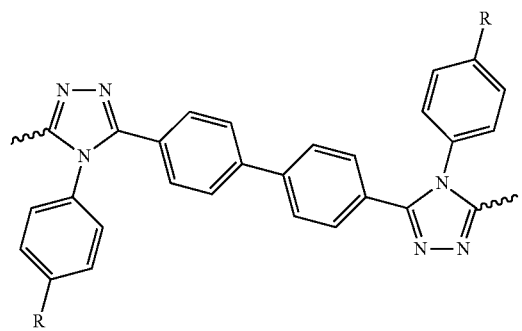
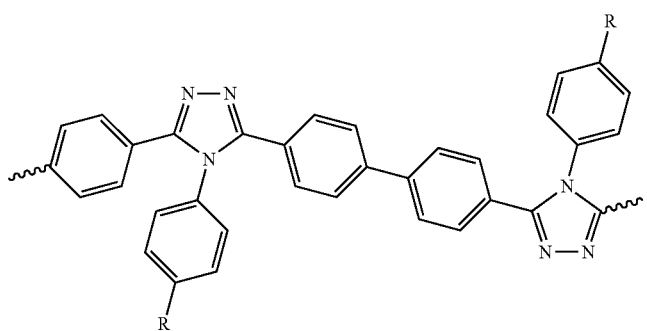
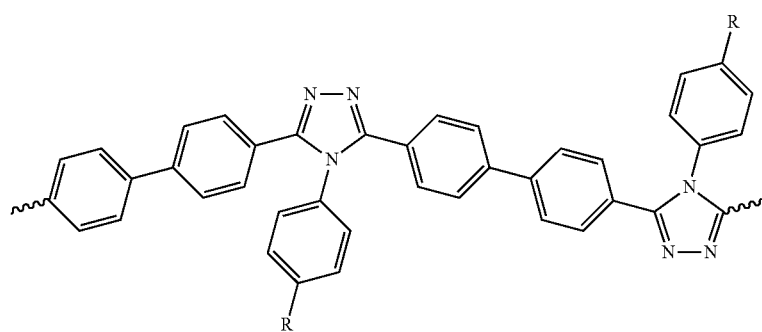
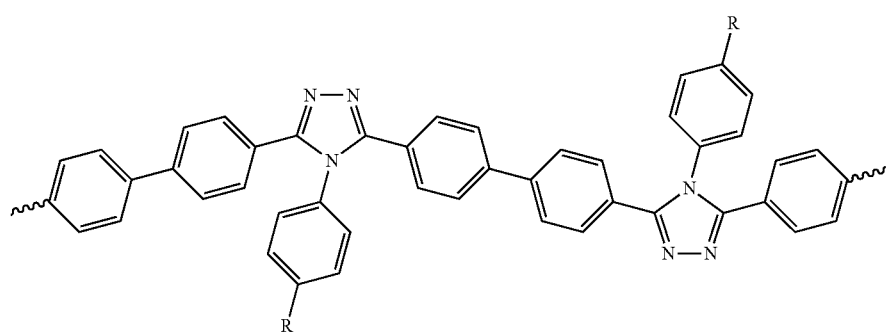

-continued
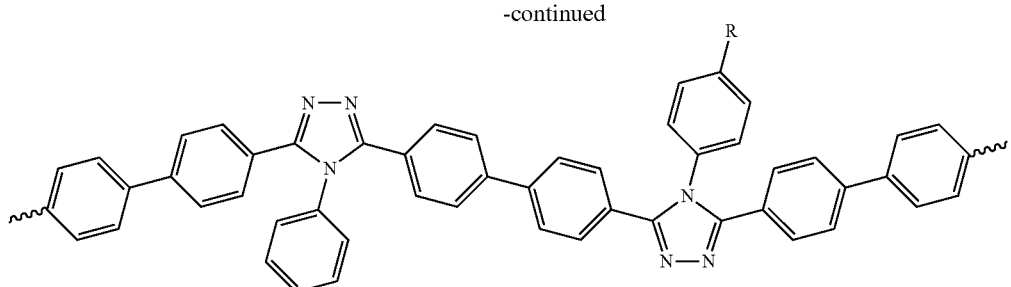
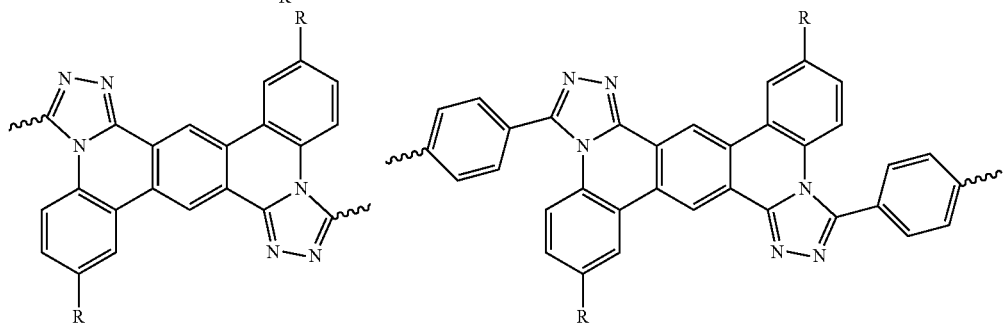
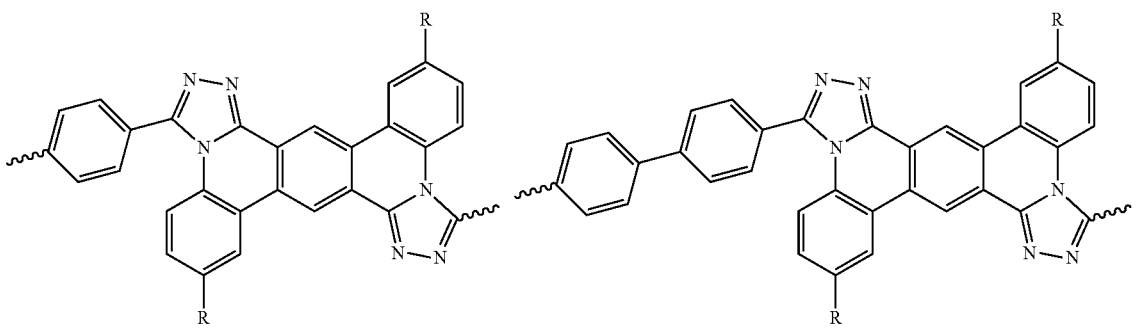
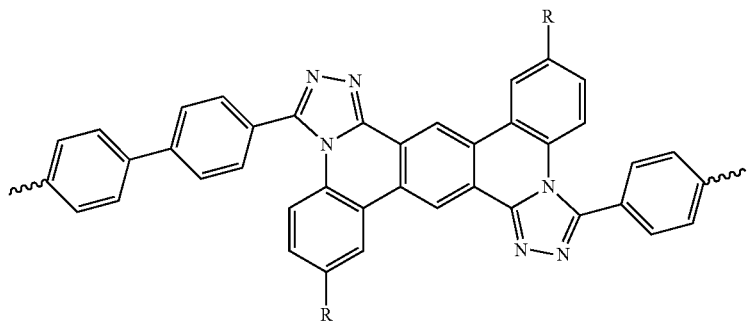
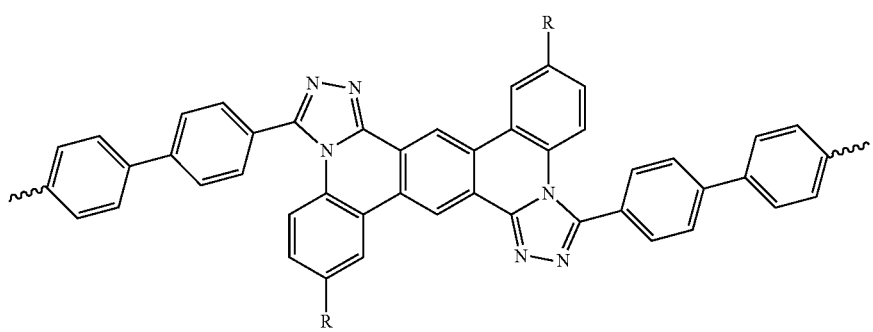

-continued
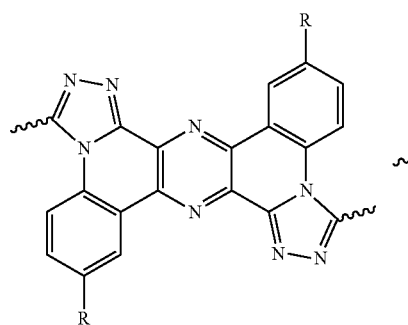
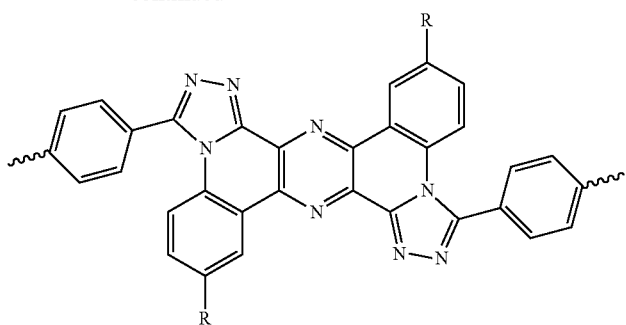
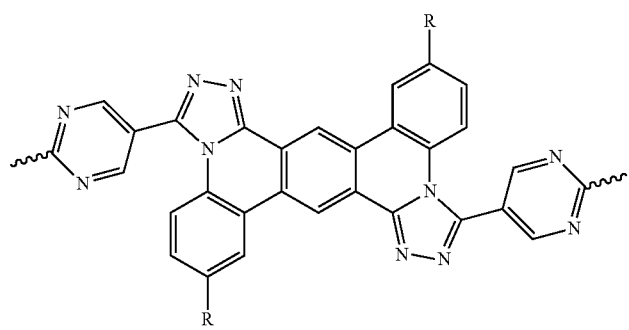
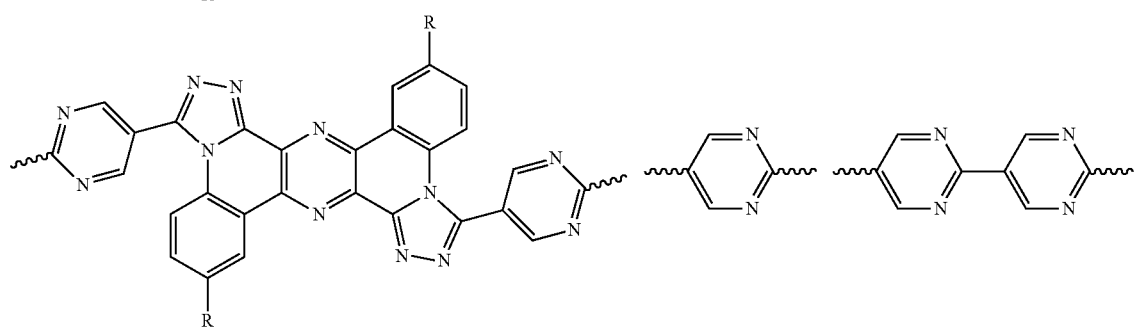
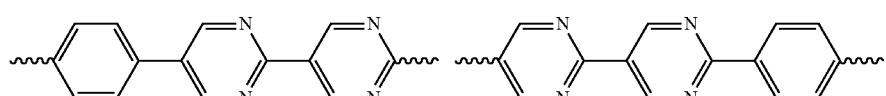
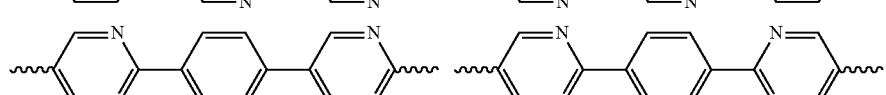
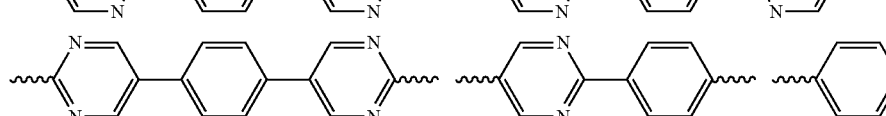
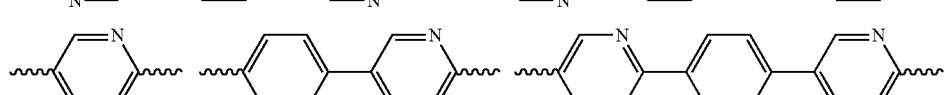
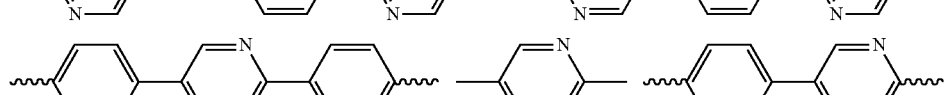
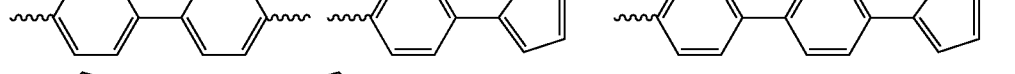

-continued
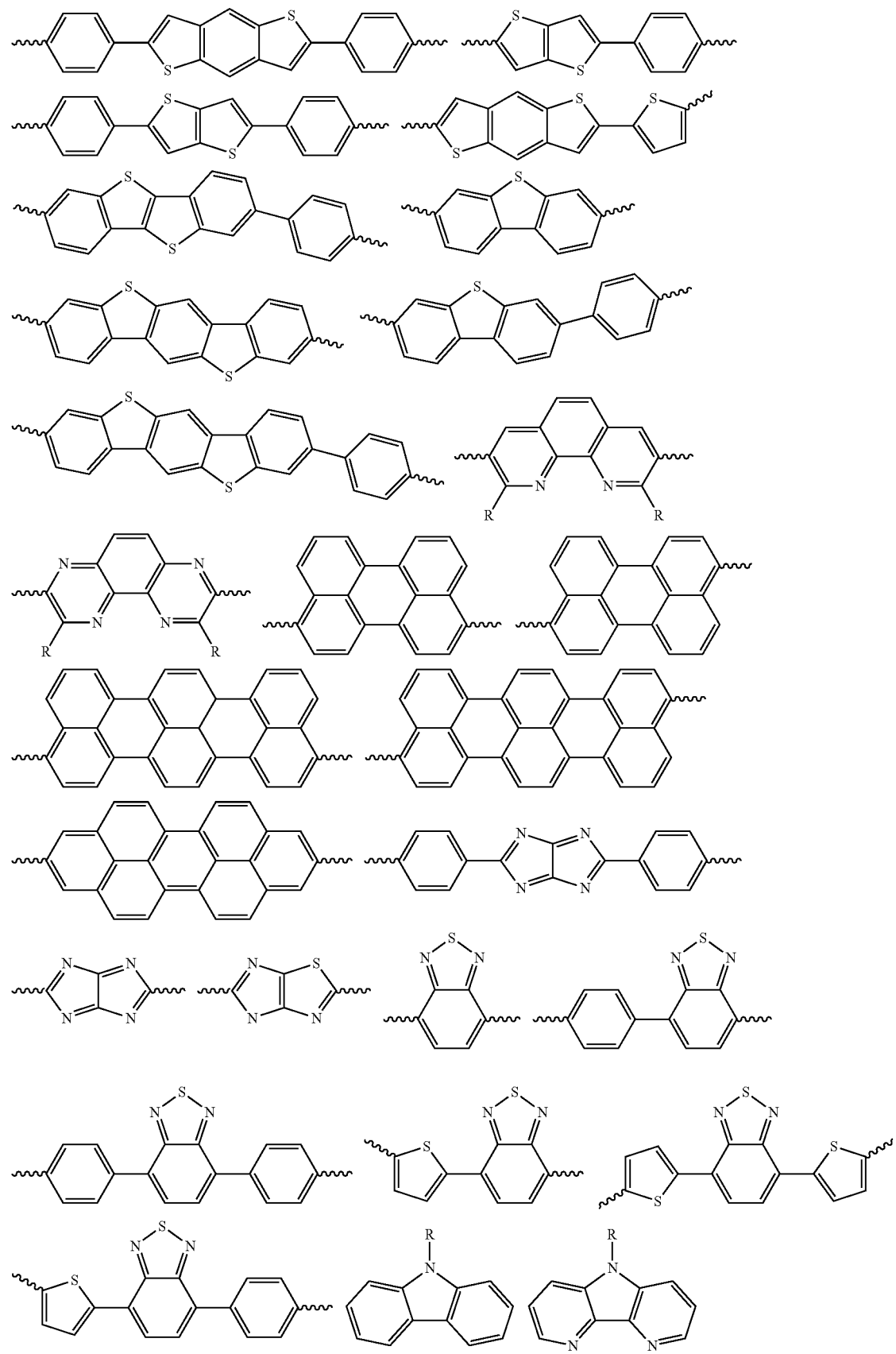

wherein R may be hydrogen, alkyl or fluoroalkyl. Further examples of E sub-units are:
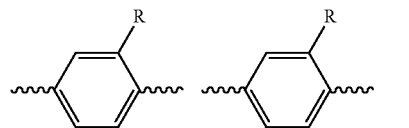
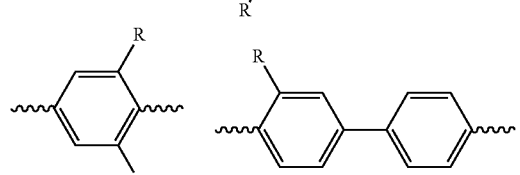
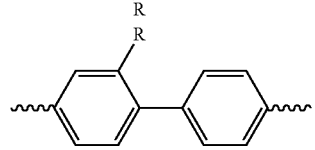
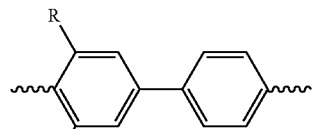
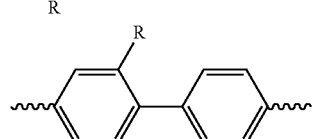
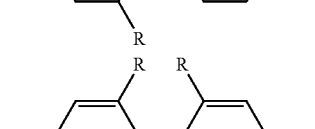
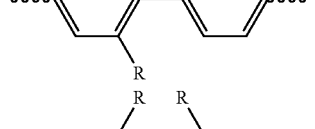
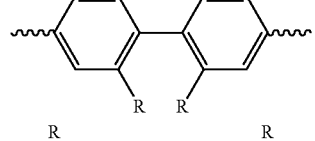
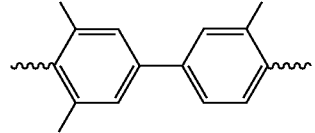
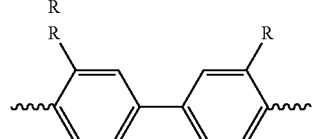
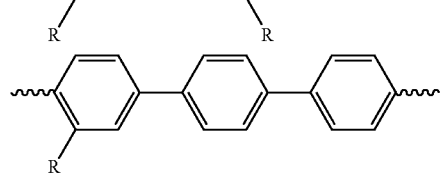
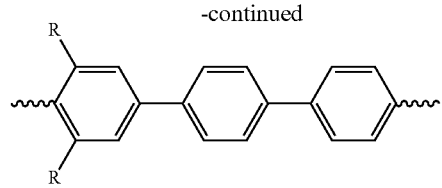
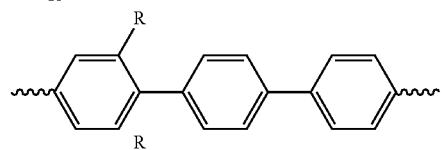
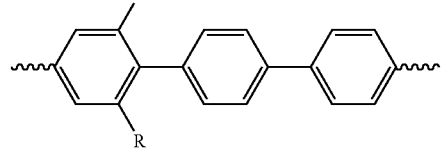
wherein R may be an alkyl or fluorinated alkyl group.
Examples of F sub-units are:
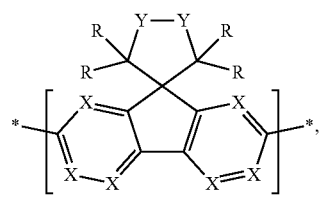
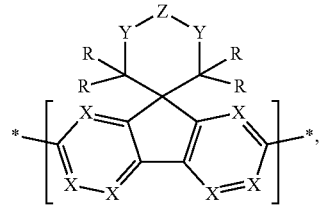
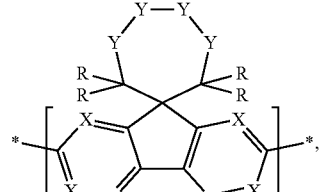
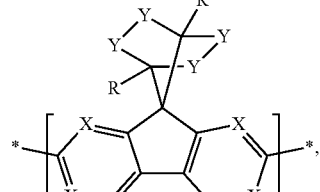
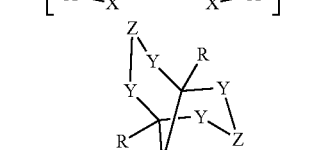
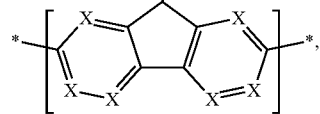

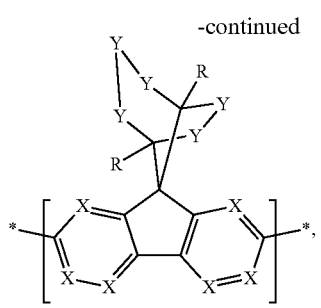
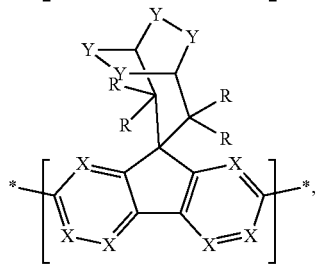
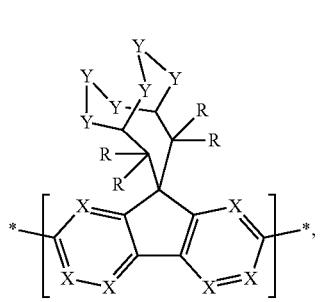
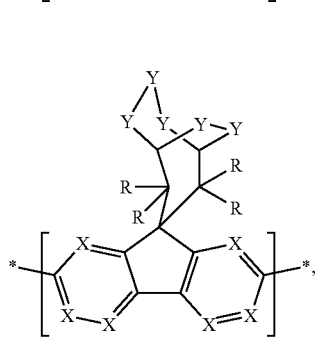
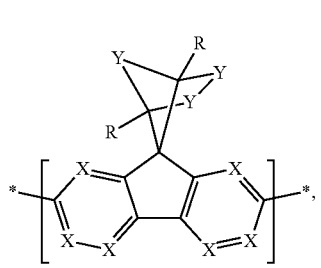
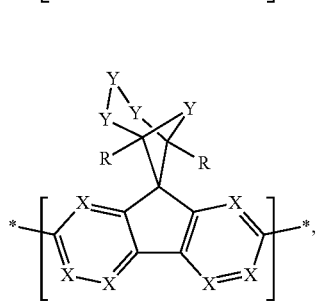
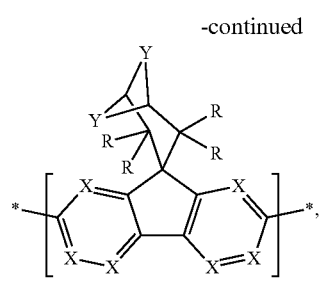
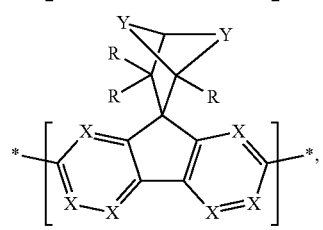
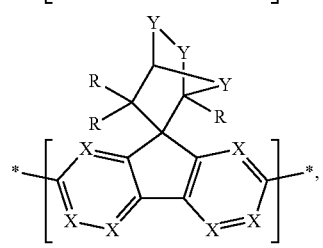
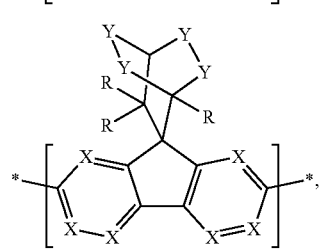
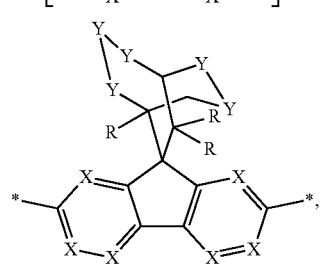
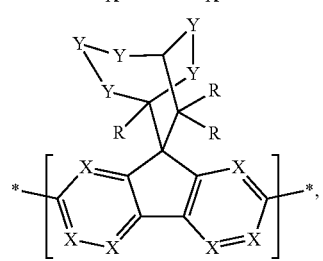
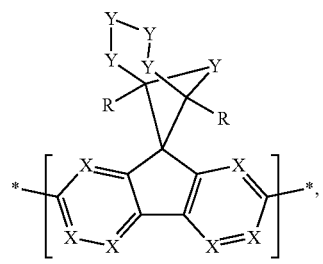

-continued

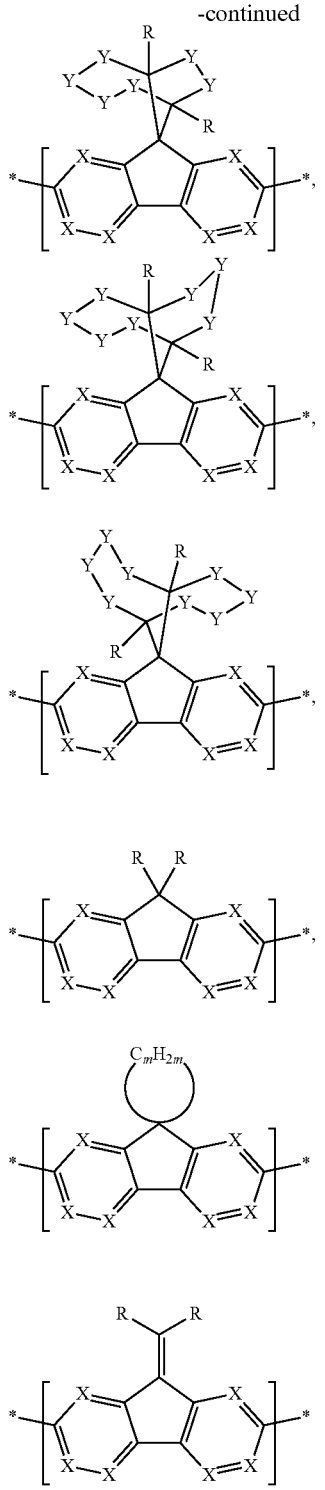

Other examples of F sub-units are:

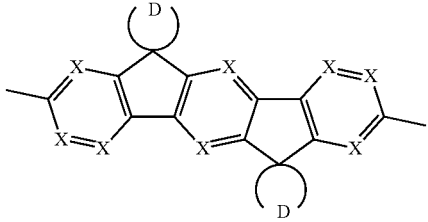
Structure 1

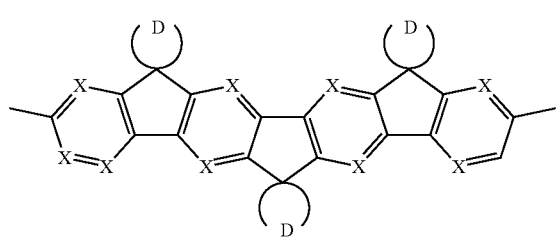
Structure 2

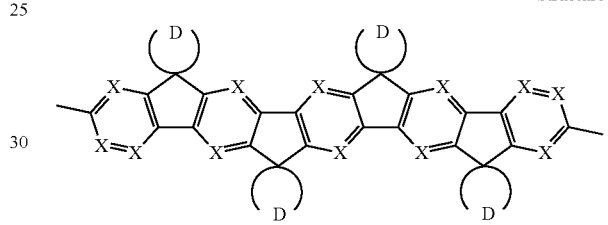
Structure 3

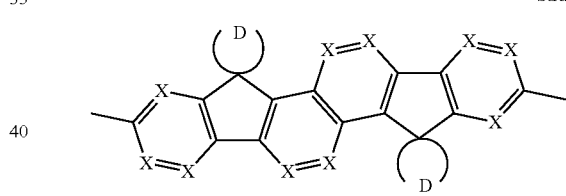
Structure 4

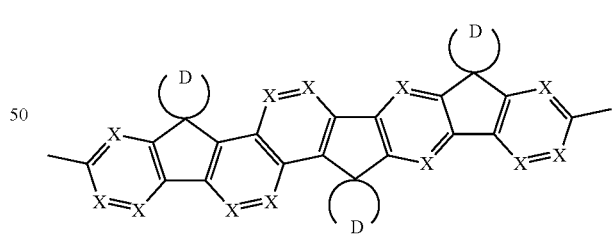
Structure 5

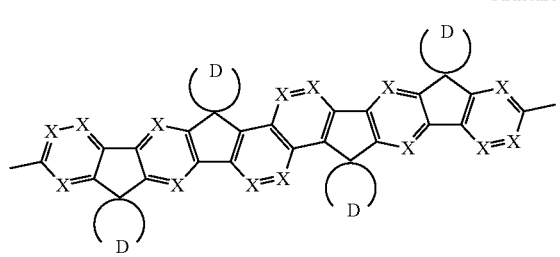
Structure 6 wherein X are chosen independently from CH, N, CR', or CF, and R'=$C_nH_{2n+1}$ where n has a value chosen independently from 1 to 5; Y and Z are chosen independently from $CH_2$, CHR", CR"$_2$, NH, NR", O, S, S=O, O=S=O, and C=O and R"=$C_nH_{2n+1}$ where n has a value chosen independently from 1 to 5; R are independently chosen from H or $C_nH_{2n+1}$ where n has a value chosen independently from 1 to 10, and m has a value between 3 and 7.

-continued
Structure 7
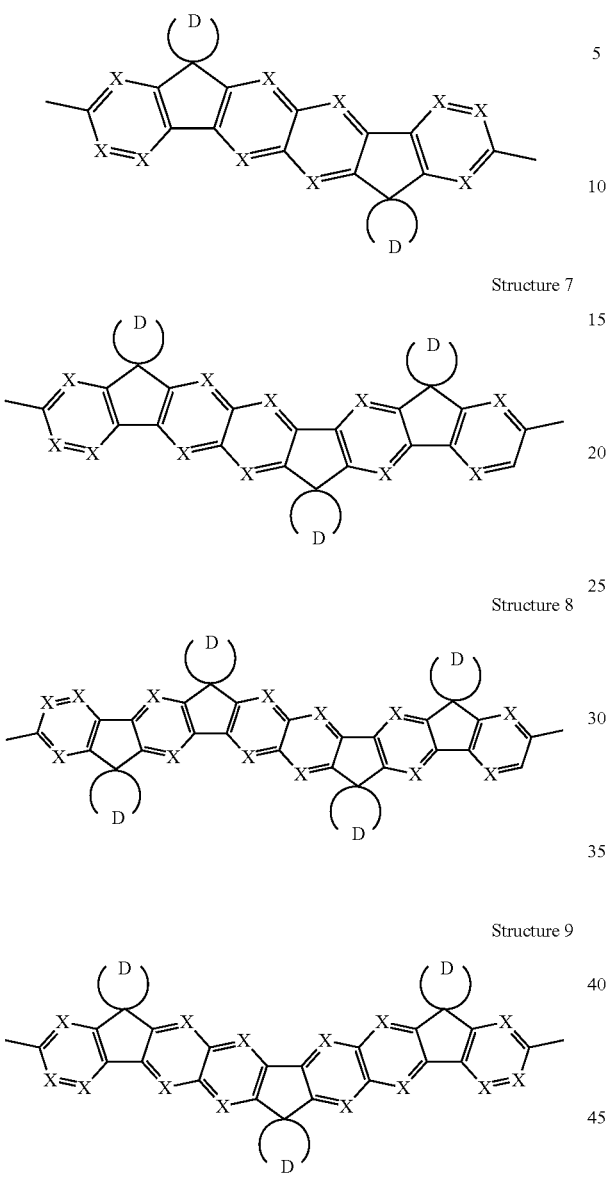
Structure 7
Structure 8
Structure 9
wherein the substituents Ⓓ may independently be one of structures:
Structure 10
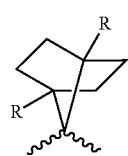
Structure 11
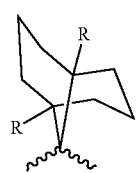
-continued
Structure 12
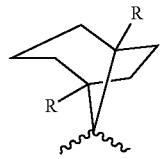
Structure 13
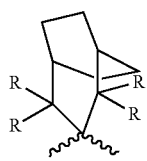
Structure 14
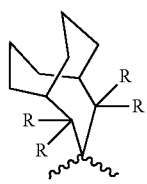
Structure 15
Structure 16
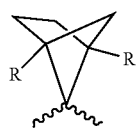
Structure 17
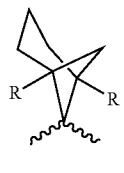
Structure 18
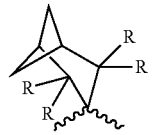
Structure 19
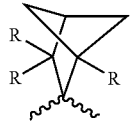
Structure 20
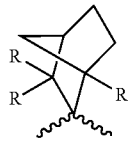
Structure 21
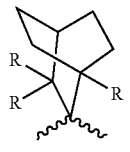

Structure 16
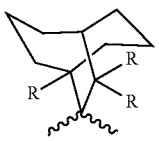

Structure 17
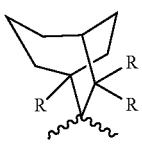

Structure 18
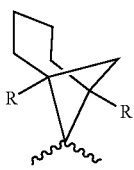

Structure 19
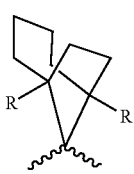

Structure 20
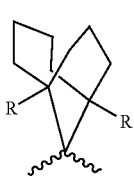

Structure 21
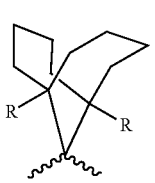

Structure 22
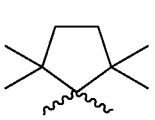

Structure 23
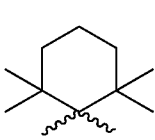

Structure 24
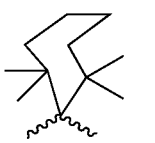

Structure 25
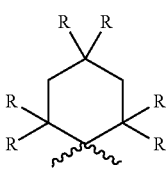

Structure 26
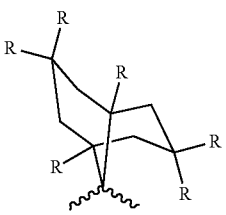

Structure 27

Structure 28
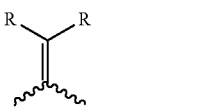

and wherein R is an alkyl group and may be chosen from methyl, ethyl, propyl, butyl, isopropyl, sec-butyl, isobutyl, tert-butyl, 2-amyl, 3-amyl, 2-methyl-2-butyl, 3-methyl-3-amyl, 3-ethyl-3-amyl, neo-pentyl, hexyl, heptyl, octyl, nonyl, or decyl and X may be independently selected from =CH—, =N—, CR', or CF, and R'=$C_nH_{2n+1}$ where n has a value chosen independently from 1 to 5.

The flexible spacer units S may be branched, straight chain, or cyclic alkyl groups with 3 to 12 carbon atoms, which are unsubstituted, or mono- or poly-substituted by F, Cl, Br, I, or CN or wherein one or more nonadjacent $CH_2$ groups are replaced by —O—, —S—, —NH—, —NR—, —SiRR—, —CO—, —COO—, —OCO—, —OCO—O—, —S—CO—, —CO—S—, —CH=CH—, —C≡C— such that O and S atoms are not directly linked to other O or S atoms.

The spacer units P separate the crosslinking groups B from each other and help determine the stiffness of the polymer matrix formed after the molecules have been crosslinked. More rigid P units, for instance those composed of aromatic rings, will lead to a stiffer, more rigid polymer. More flexible P spacers, for instance simple alkyl chains, will result in a softer more deformable polymer matrix. Altering the characteristics of the P spacers can be used to "tune" the characteristic of the resulting polymer matrix film.

A further aspect of the invention is that mixtures of materials with varying length spacers may be used to destabilise the more highly ordered smectic phases in favour of the nematic phase if that is desired.

Examples of spacer groups (P) are:

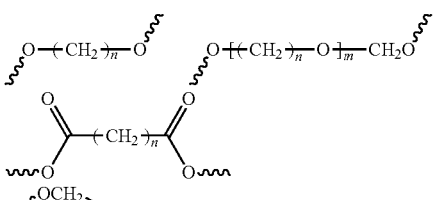

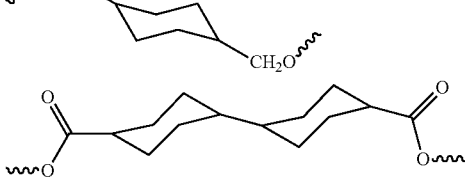

-continued

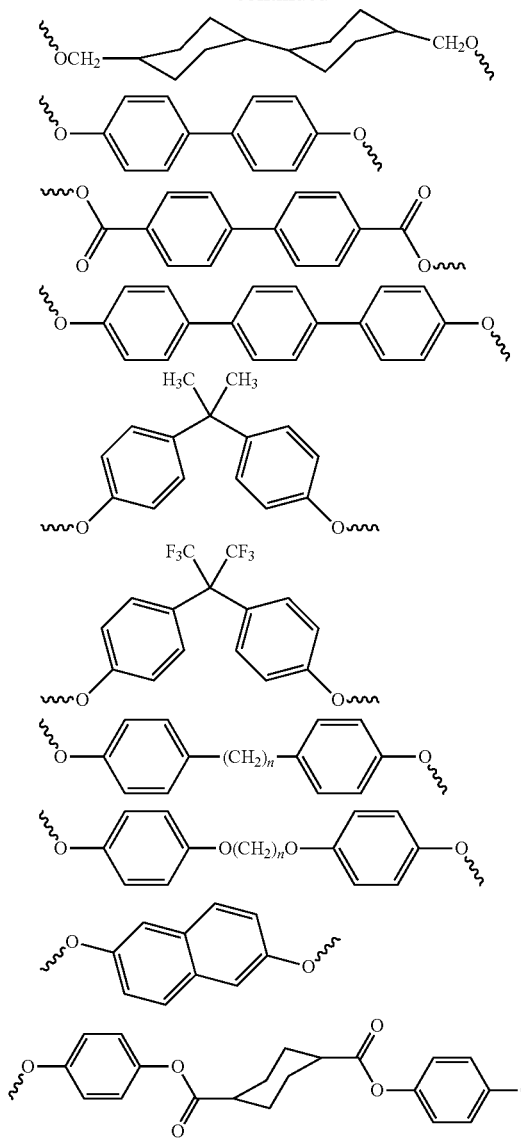

Crosslinking group (B) may be any crosslinking group so long as it is difunctionalised such that it may be incorporated in the backbone of the molecule, for instance:

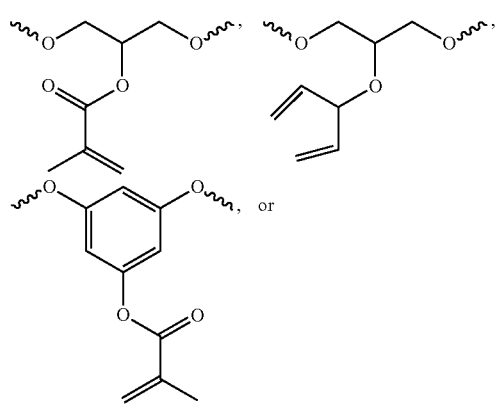

-continued

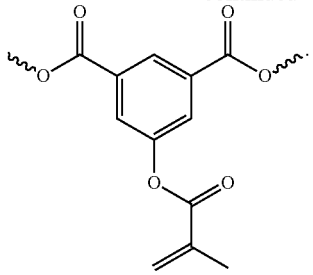

Mixtures may be used of two or more molecules in at least one of which the crosslinking units are electron deficient and in at least another one of which the crosslinking units are electron rich. In mixtures of this type crosslinking proceeds by way of electron transfer polymerization. Crosslinking liquid crystalline materials using this technique for use in OLEDs and other organic electronics has previously been described in patent application WO2007064721.

Examples of electron deficient crosslinking groups that may serve as the B group in the invention are:

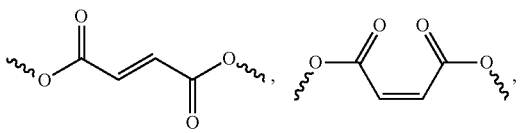
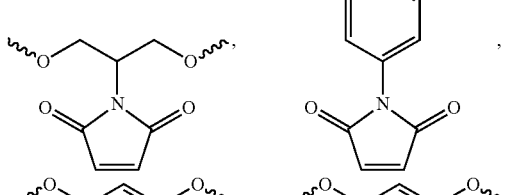
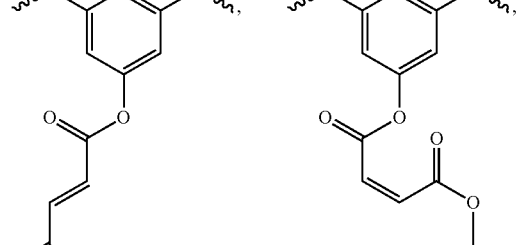
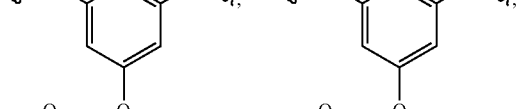

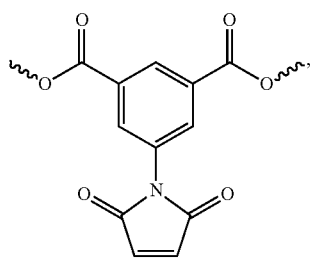
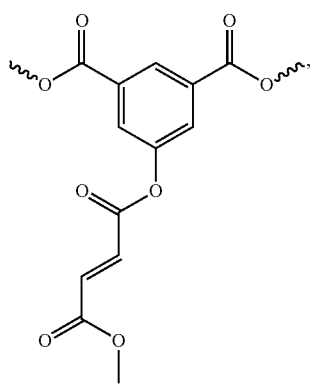
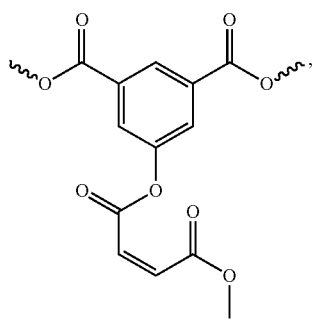
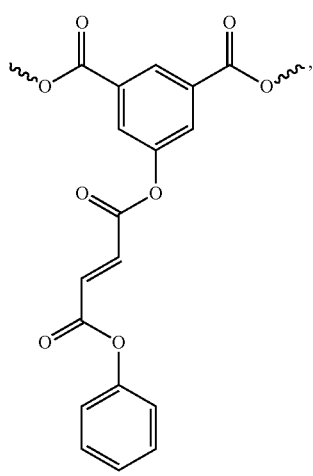
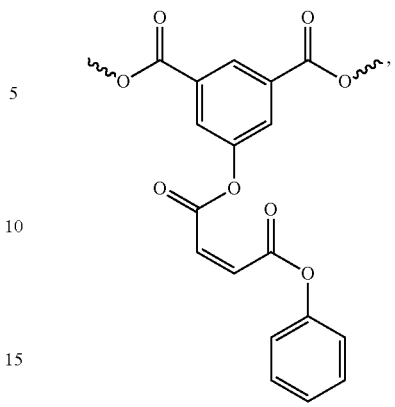
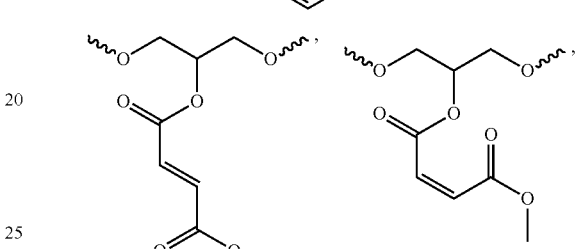
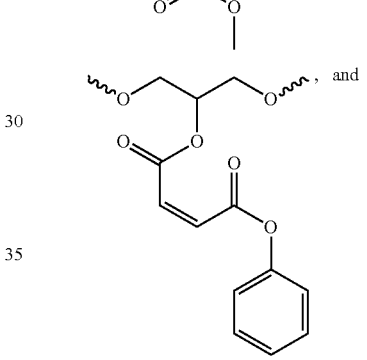
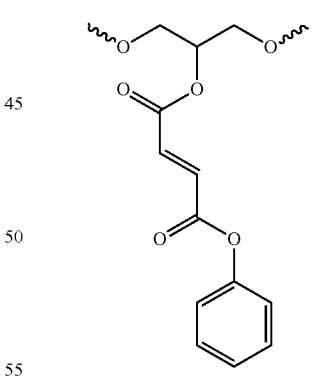
Examples of electron rich crosslinking groups that may serve as the B group in the invention are:
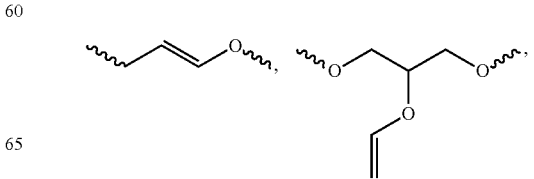

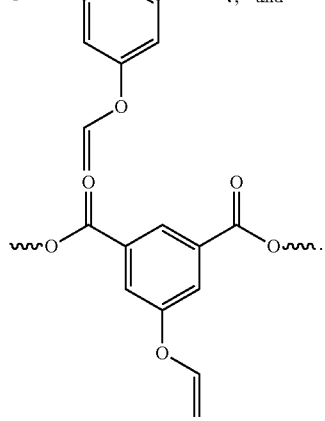

The end groups T may be chosen from hydrogen, an alkyl chain, an alkoxy chain, a cyano group or a fluorine. The alkyl and alkoxy chains may comprise branched, straight chain, or cyclic alkyl groups with 1 to 12 carbon atoms, which are unsubstituted, or mono- or poly-substituted by F, Cl, Br, I, or CN or wherein one or more nonadjacent $CH_2$ groups are replaced by —O—, —S—, —NH—, —NR—, —SiRR—, —CO—, —COO—, —OCO—, —OCO—O—, —S—CO—, —CO—S—, —CH=CH—, —C≡C— such that O and S atoms are not directly linked to other O or S atoms. The alkyl or alkoxy chains may be terminated with crosslinking groups. Examples of these terminal crosslinking groups are:

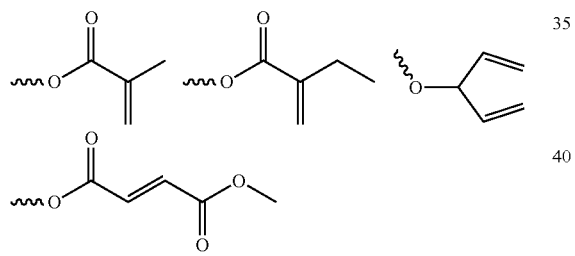

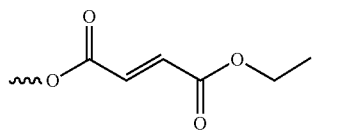
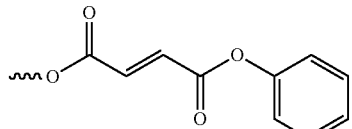
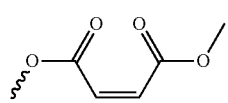
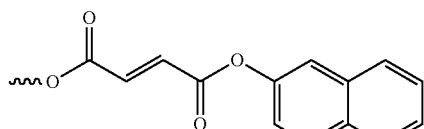
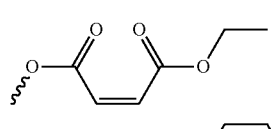
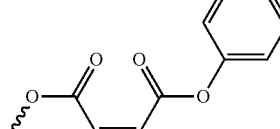
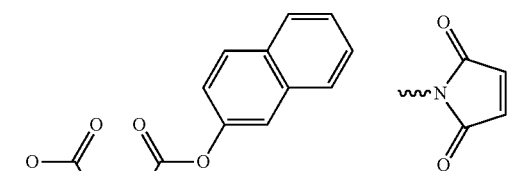

Examples of molecular structures of the inventive materials are:

Structure 29

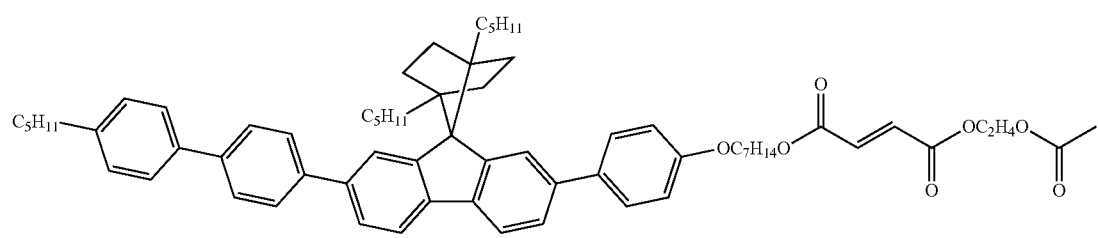

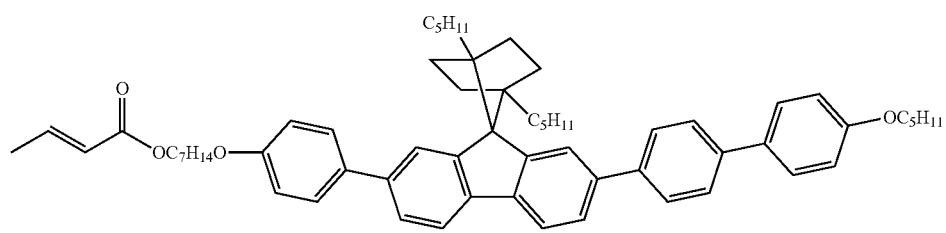

-continued
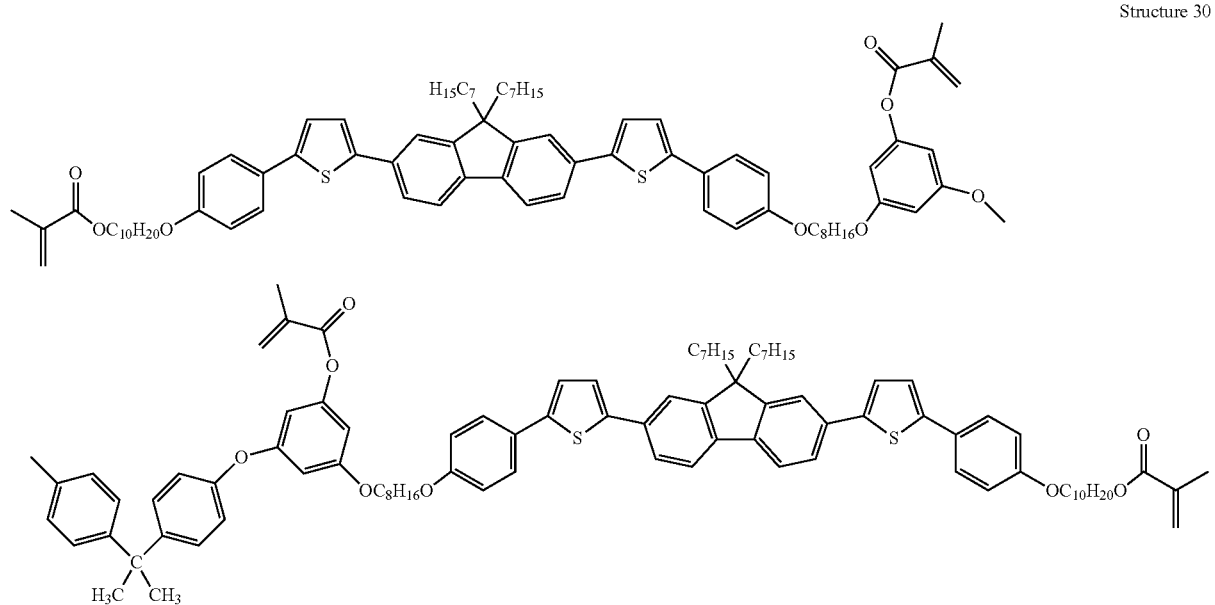
Structure 30
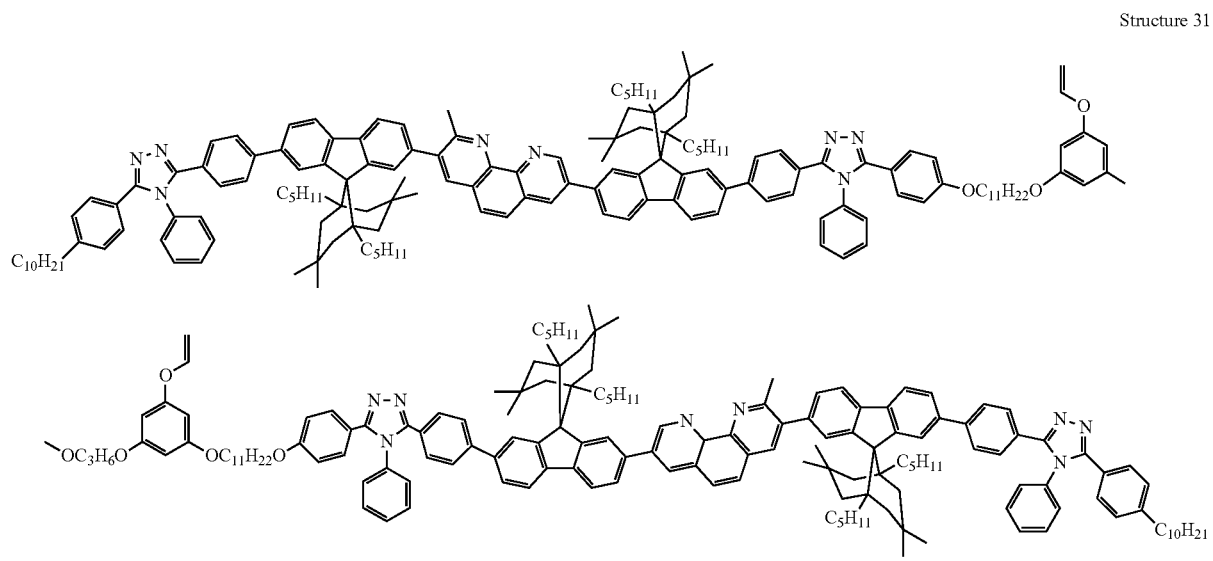
Structure 31
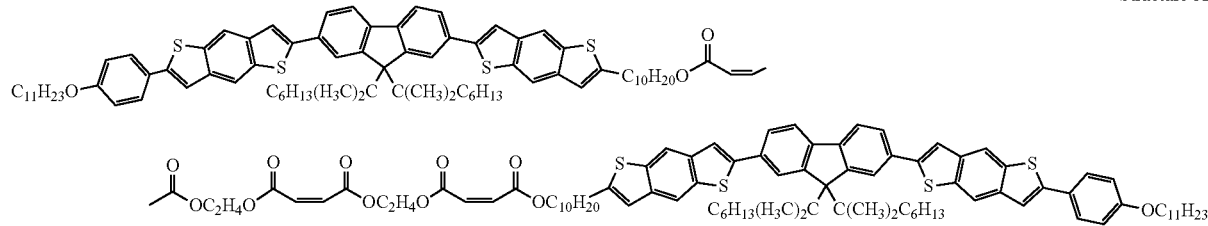
Structure 32
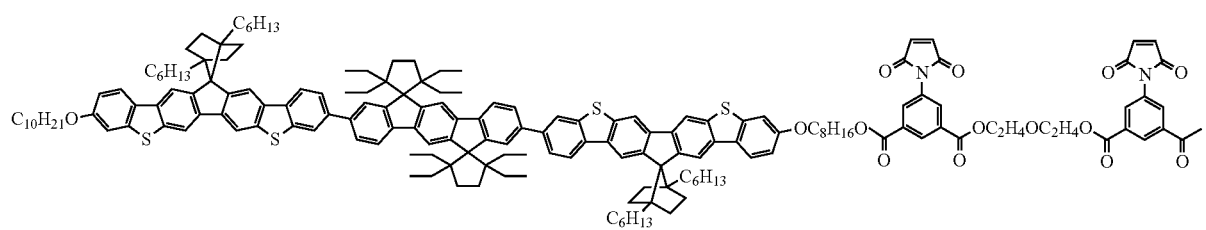
Structure 33

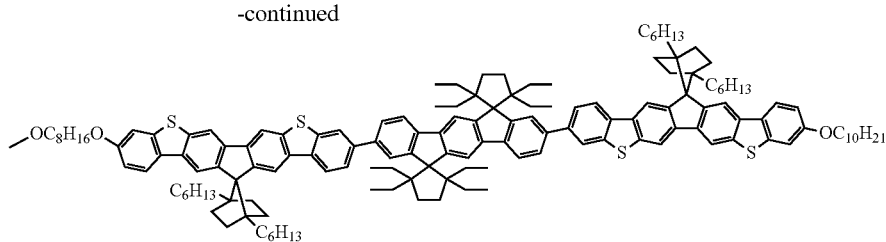

Structure 34

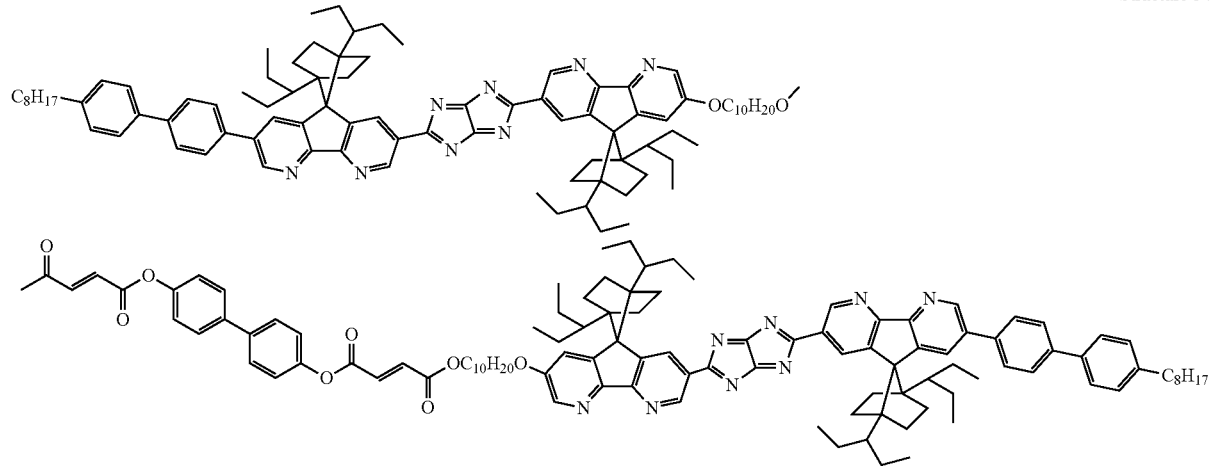

Structure 35 = (A)₂B
wherein:

A =

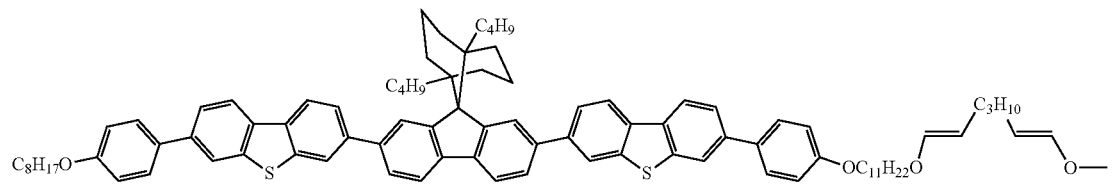

B =

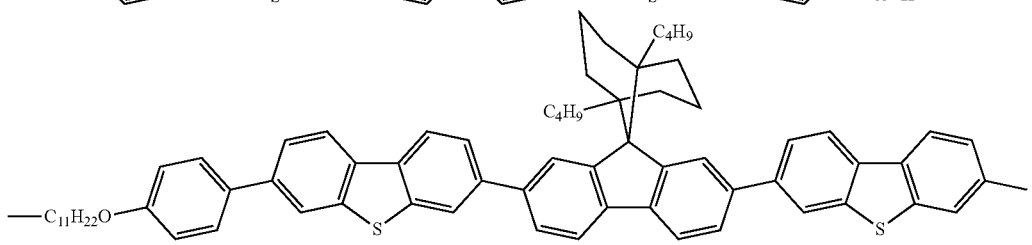

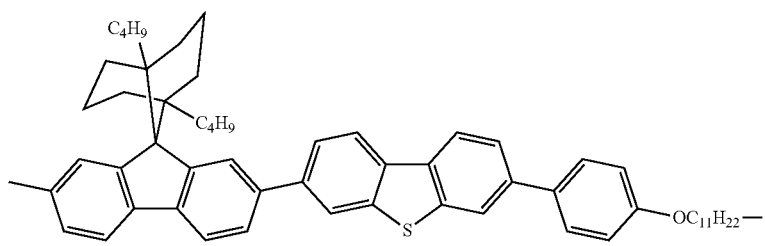

Compounds with structures 29, 30, 31, 33, and 34 in which m=n=1 are, in general preferred because they are simpler and less expensive to prepare.

Since the -S-B-P-B-S- structure will, in general, be easily prepared and therefore less expensive than adding on additional aromatic rings in the molecular core units, the inventive compounds provide a method to increase molecular weight and to enhance the film forming characteristics of solutions of the materials with minimal impact to the cost of manufacture. In addition, the length of the molecule is increased without substantially altering chromophoric properties of the molecular core. The capability can prove most useful when developing host materials that require relatively short wavelength luminescence bands to be compatible with guest emitter materials.

In another embodiment of the invention the crosslinking (B) and spacer (P) functionalities can be combined in a single structural sub-unit of the molecule. Some examples of these sorts of structures are:

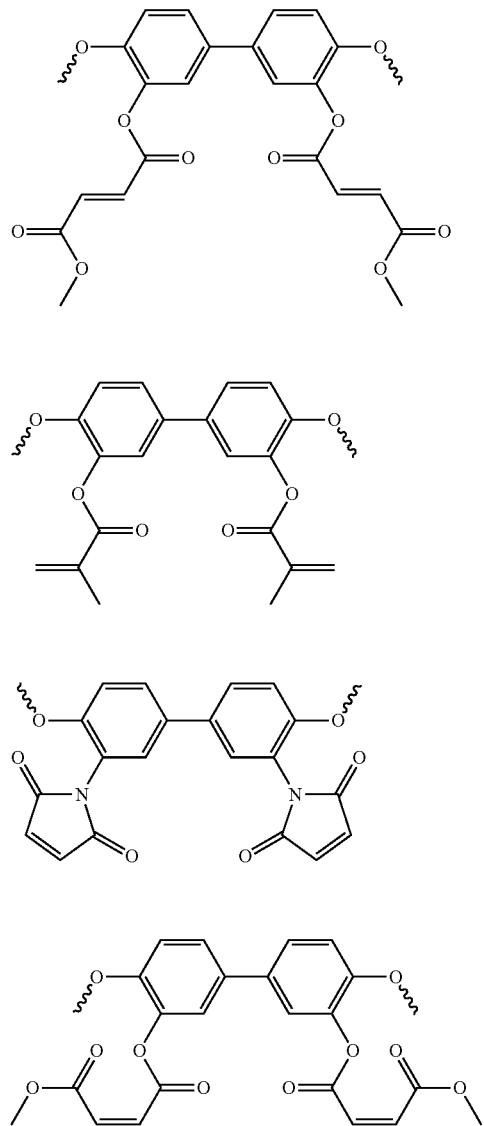

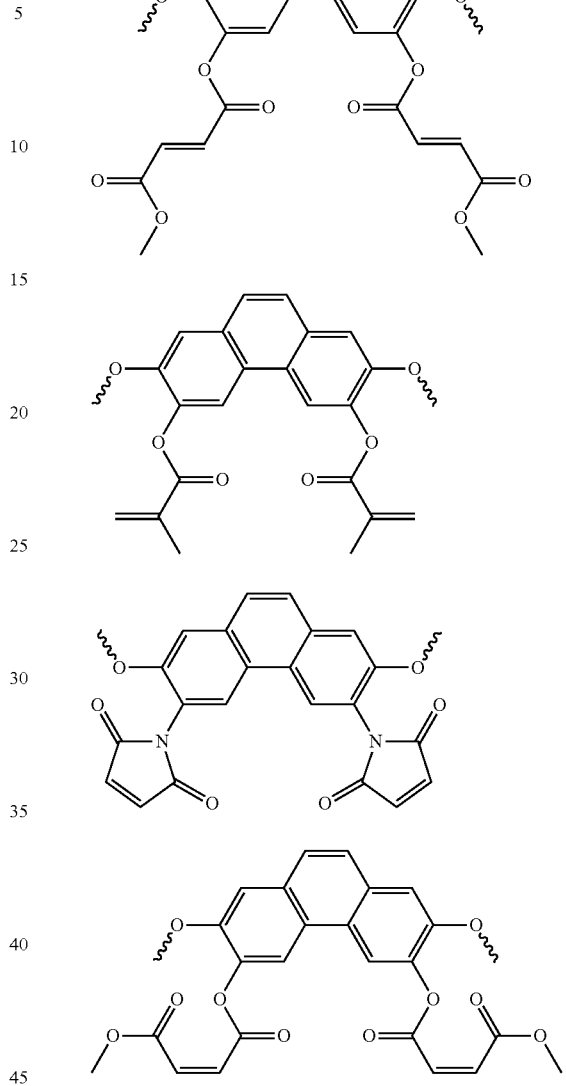

In another embodiment of the invention, materials having the formula:

T-A(-S-B(-P-B)$_m$-S-A)$_n$-T may be mixed with the prior art materials having the formulae B-S-A-S or B-S-A-S-B.

For instance one equivalent of material having the structure 29 from above:

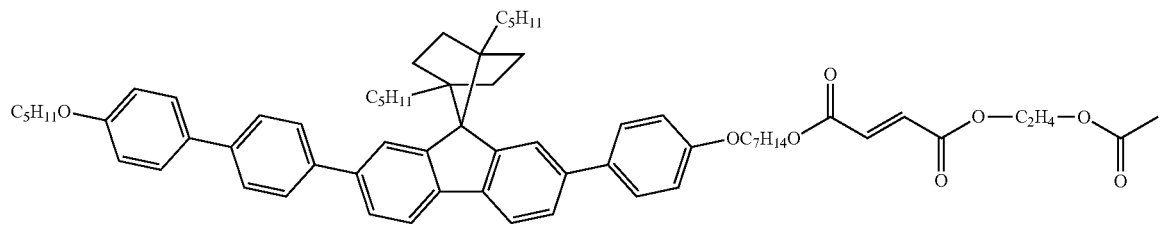

-continued

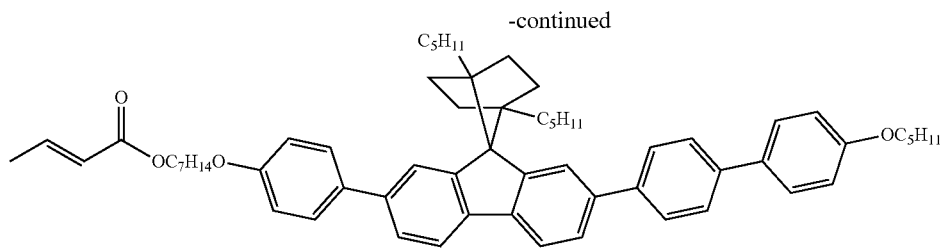

could be mixed with two equivalents of material consisting of 3 mole % of a compound with formula:

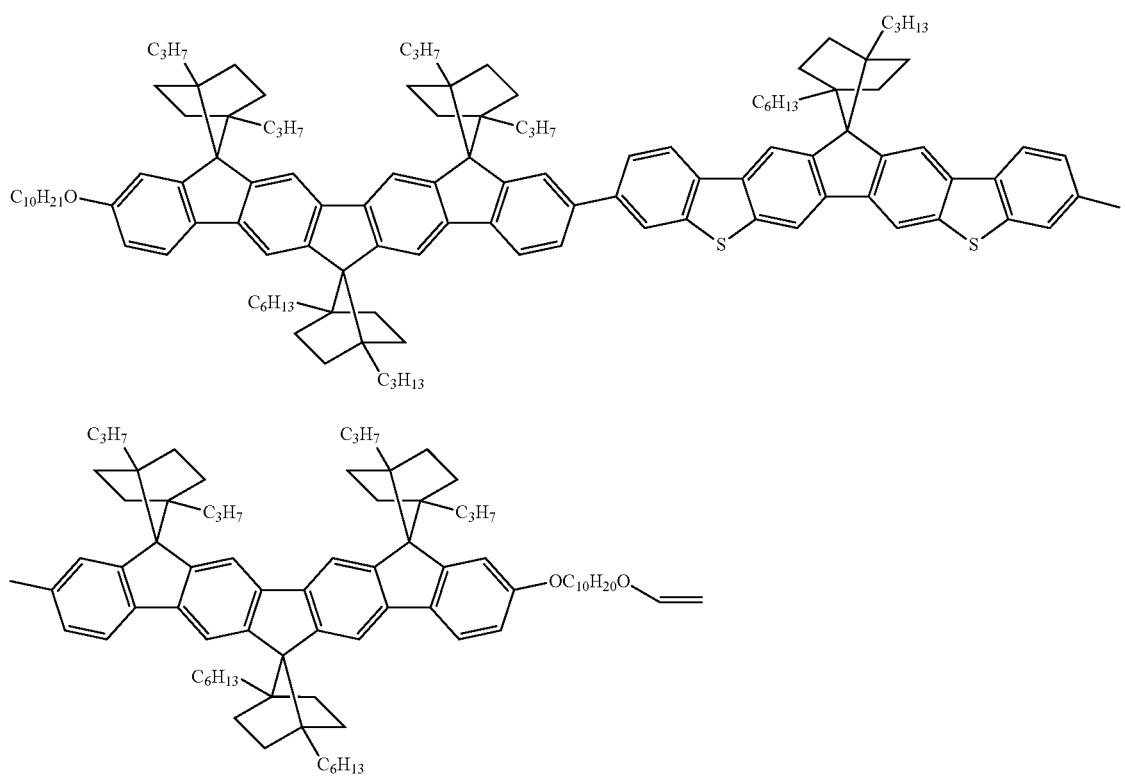

and 97 mole % of a compound with formula:

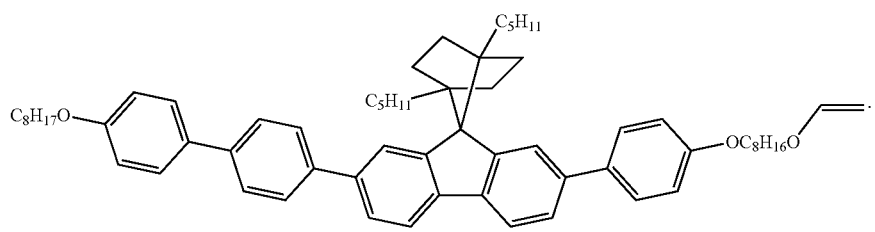

The material is then coated down and polymerized to form the copolymer.

In yet a further embodiment of the invention, material having structure 29, for example, may be copolymerised with a non-liquid crystalline monomer, for instance:

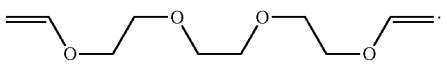

This provides a method of producing a polymer matrix film by the electron transfer polymerization method while only using only single liquid crystalline material of the invention.
An exemplary synthesis follows:
Compounds Used for Exemplary Synthesis
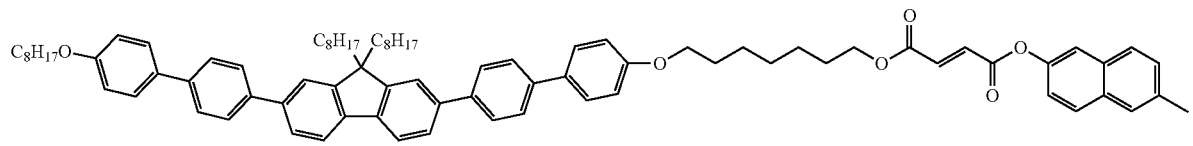
Compound 1
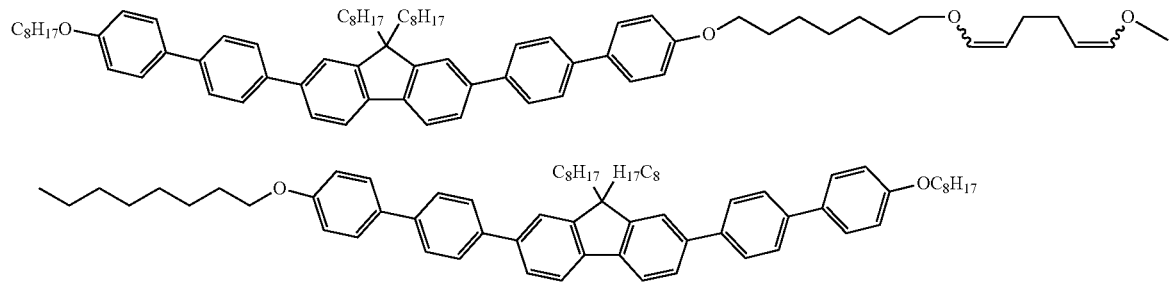
Compound 2
35
Synthesis of Compound 1
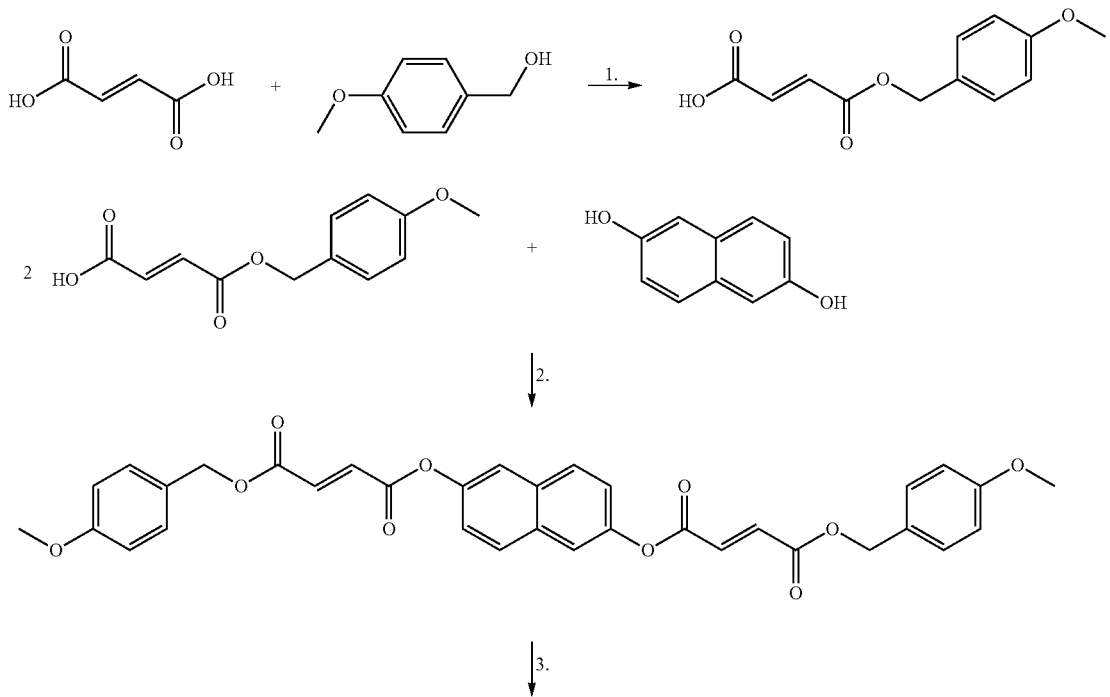

-continued

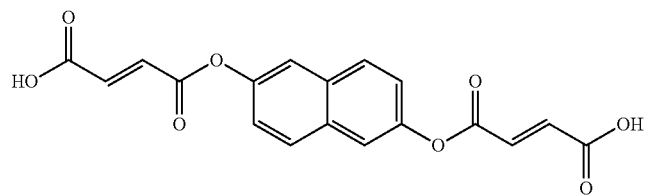

1. Dicyclohexylcarbodiimide and catalytic 4-dimethylaminopyridine in dimethylformamide solvent overnight at room temperature,
2. Dicyclohexylcarbodiimide and catalytic 4-dimethylaminopyridine in dimethylformamide solvent overnight at room temperature,
3. Equimolar trifluoroacetic acid in phenol as the solvent at 45 degress C. for one hour

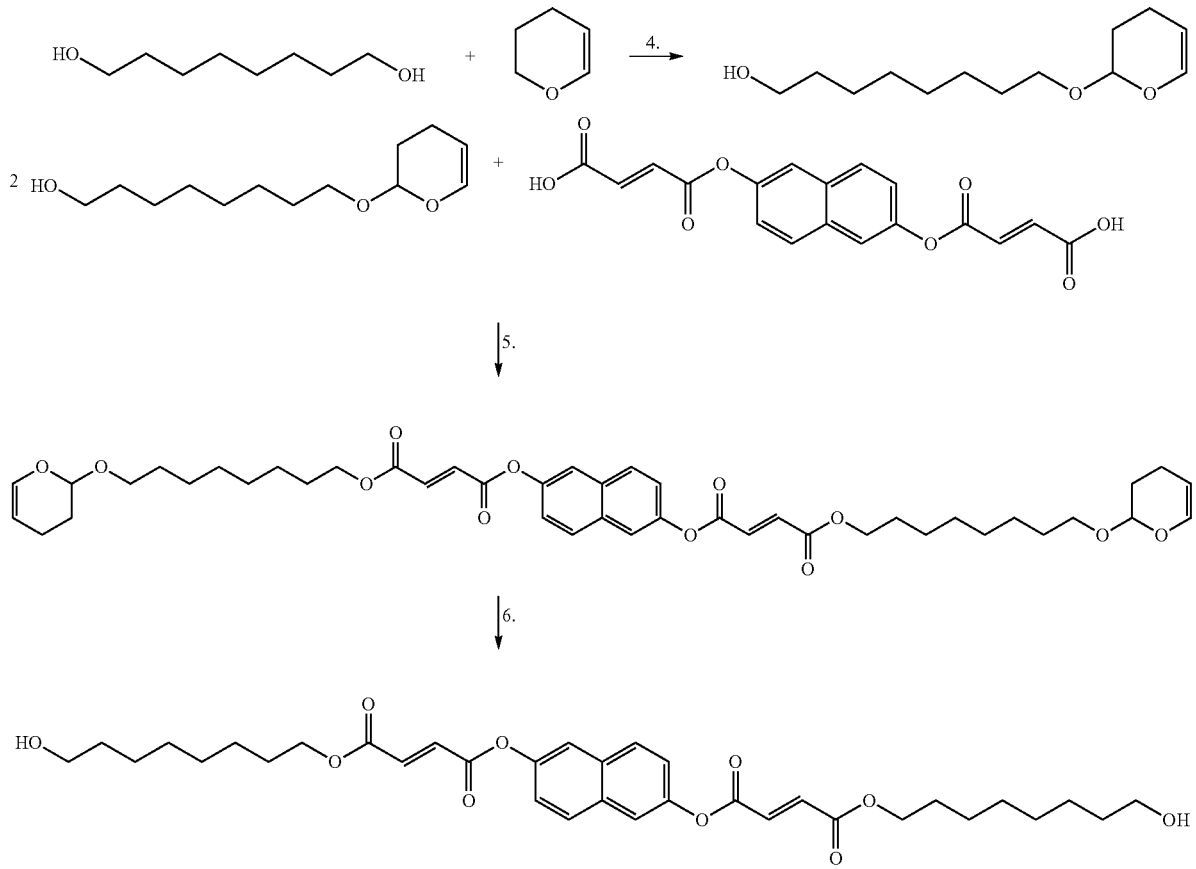

4. Excess dihydropyran with catalytic camphorsulfonic acid at 65 degrees C. for 3.5 hours
5. Dicyclohexylcarbodiimide and catalytic 4-dimethylaminopyridine in dimethylformamide solvent overnight at room temperature
6. 95% acetic acid/5% water for six hours

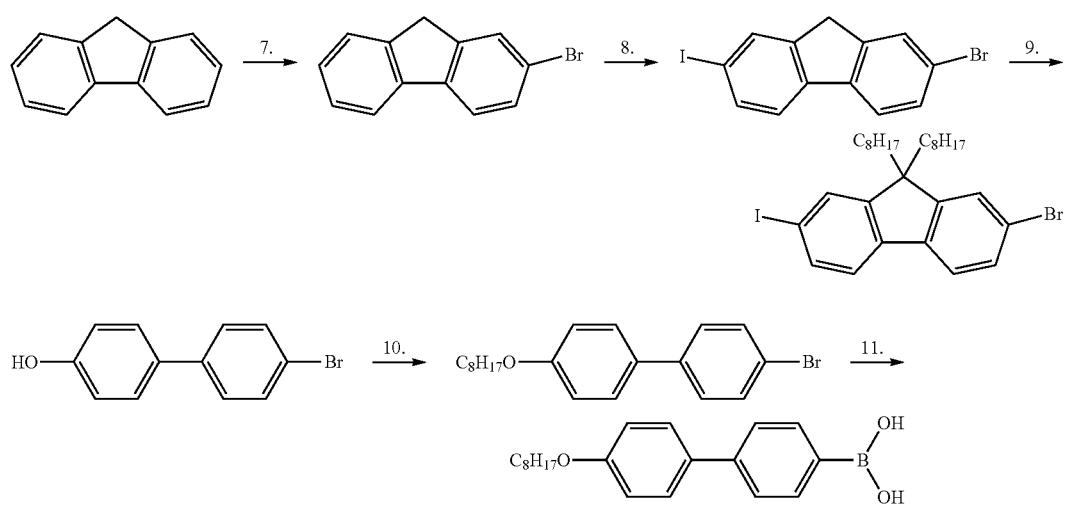

-continued

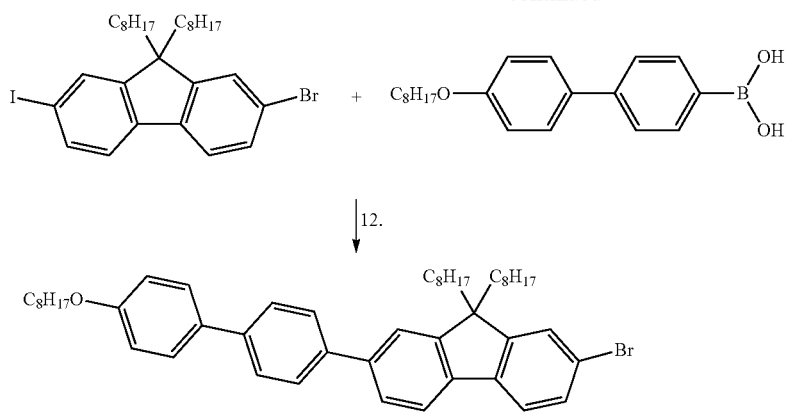

7. Equimolar bromine in chloroform solvent at room temperature under nitrogen for one hour
8. Iodine, potassium iodate, acetic acid, H₂O
9. i. KOH in DMSO solvent at 5-10 degrees C. for two hours, ii. C₈H₁₇Br overnight at 5-10 degrees C.
10. C₈H₁₇Br, K₂CO₃, catalytic tetrabutylammonium bromide in 2-butanone refluxed overnight
11. i. n-Butyl lithium in dry THF solvent for one hour at -78 degrees C., ii. Trimethyl borate at -78 degrees C., warm to RT overnight
12. K₂CO₃, Pd(PPh₃)₄, toluene:H₂O (2:1)

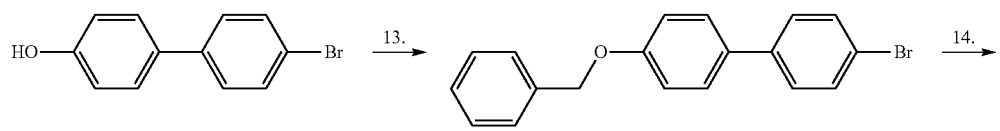

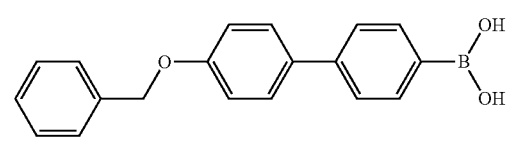

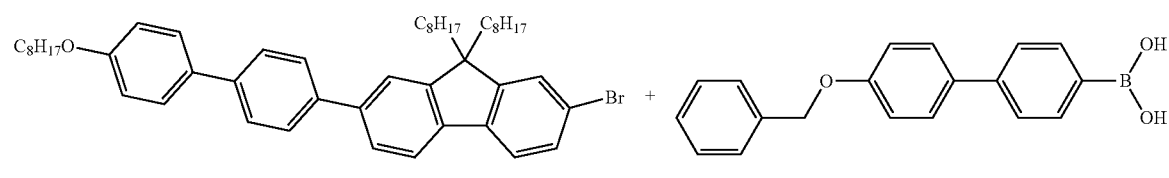

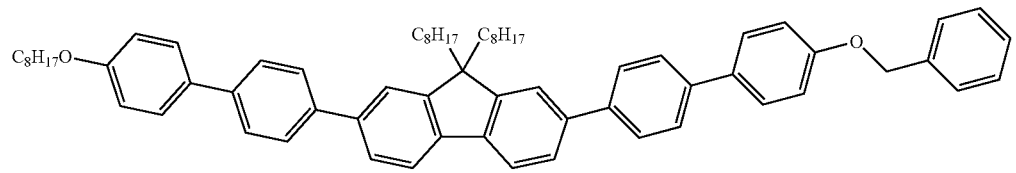

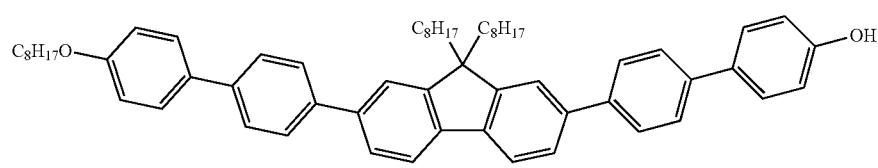

13. Benzyl bromide, K₂CO₃, catalytic tetrabutylammonium bromide in 2-butanone refluxed overnight
14. i. n-Butyl lithium in dry THF solvent for one hour at -78 degrees C., ii. Trimethyl borate at -78 degrees C., warm to RT overnight
15. K₂CO₃, Pd(PPh₃)₄, toluene:H₂O (2:1)
16. 5% Pd/H₂ on carbon in THF solvent overnight

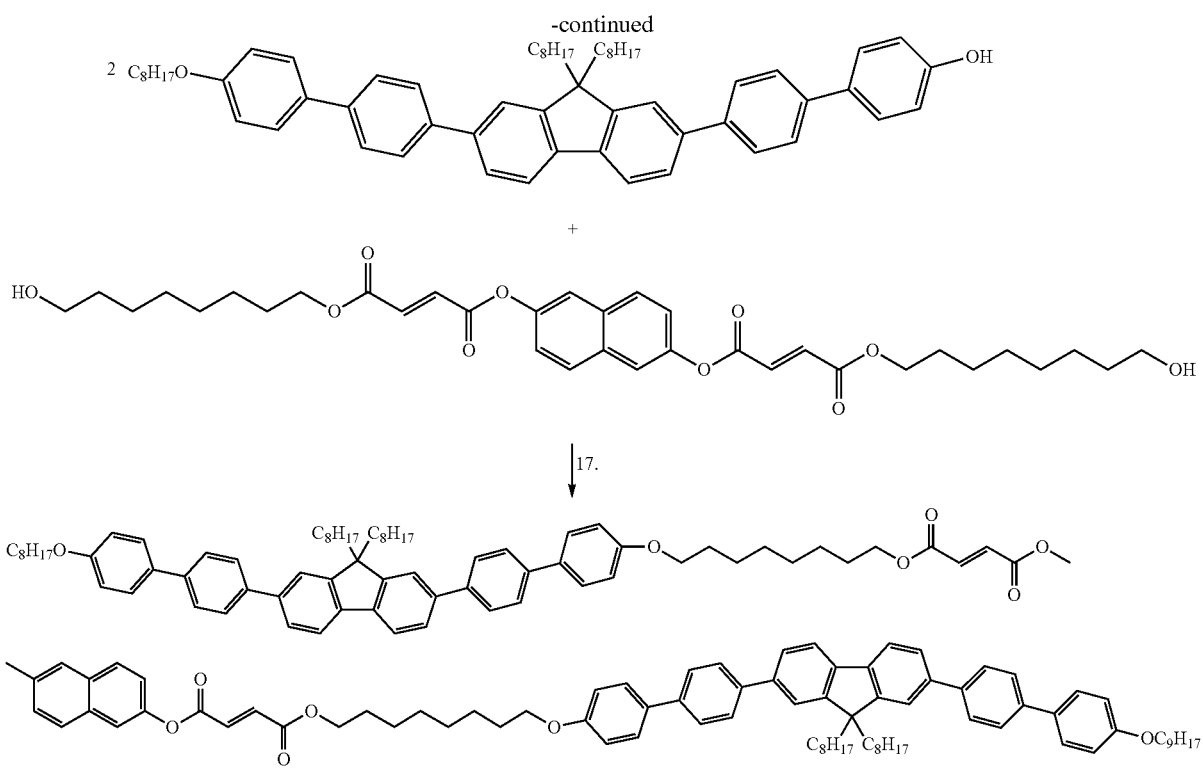

17. C$_8$H$_{17}$Br, K$_2$CO$_3$, catalytic tetrabutylammonium bromide in 2-butanone refluxed overnight Synthesis of Compound 2

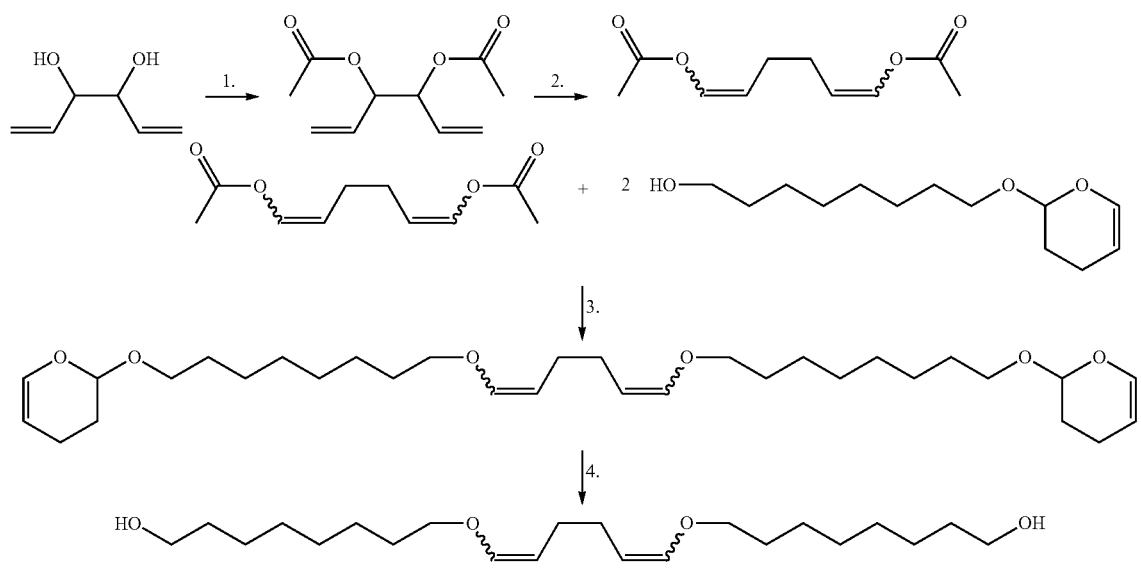

1. Acetic anhydride in pyridine solvent at 0 degrees C. then let warm to RT with stirring overnight
2. Reflux for two hours at 240 degrees C.
3. Na$_2$CO$_3$ and catalytic [Ir(COD)Cl]$_2$ in dry toluene solvent under N$_2$ refluxed overnight
4. 95% acetic acid/5% water for six hours

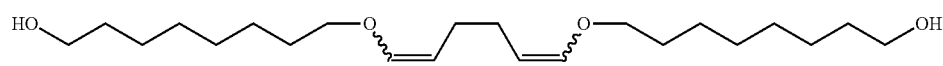

+ 2

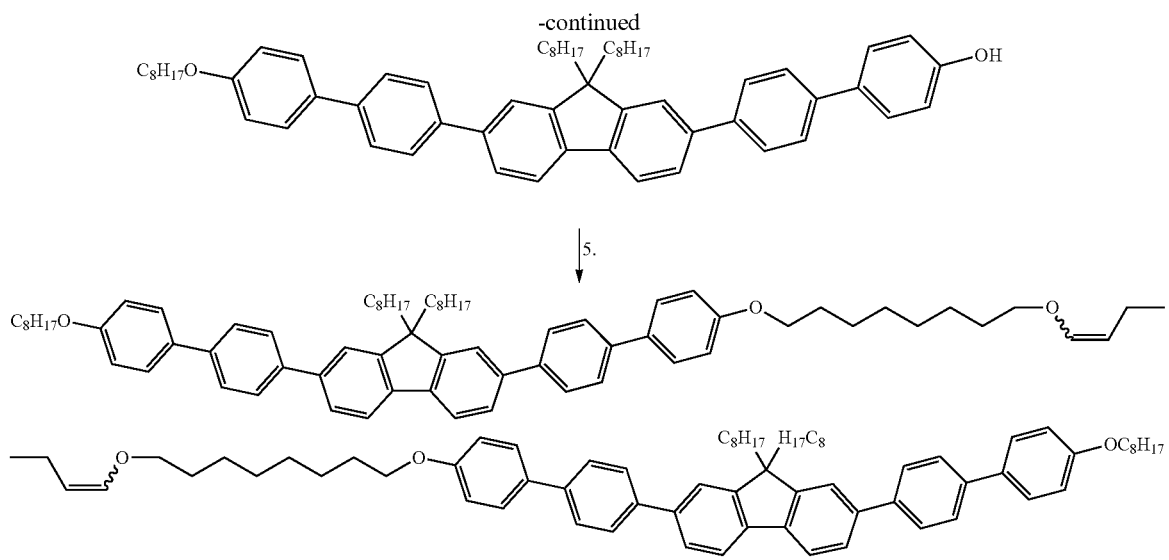

↓ 5.

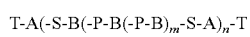

5. C$_8$H$_{17}$Br, K$_2$CO$_3$, catalytic tetrabutylammonium bromide in 2-butanone refluxed overnight

The invention claimed is:

1. An OLED comprising materials having the formula:

T-A(-S-B(-P-B(-P-B)$_m$-S-A)$_n$-T where

A are independently selected rod-shaped, rigid molecular core units having the general structure:

-E-F-(E-F)$_x$-E- wherein E is independently chosen from a single bond or an aromatic diradical disubstituted so as to maintain the linear nature of rigid molecular core A, wherein F is a diradical containing a fluorene, an azafluorene or a polyazafluorene aromatic ring system and which is disubstituted so as to maintain the linear nature of the rigid molecular core A, and wherein x is between 0 and 7, S are independently selected flexible spacer units which are branched, straight chain, or cyclic alkyl groups with 3 to 12 carbon atoms, which are unsubstituted or mono- or poly-substituted by F, Cl, Br, I, or CN or wherein one or more nonadjacent CH$_2$ groups are replaced by —O—, —S—, —NH—, —NR—, —SiRR—, —CO—, —COO—, —OCO—, —OCO—O—, —S—CO—, —CO—S—, —CH=CH—, —C≡C— such that O and S atoms are not directly linked to other O or S atoms, B are independently selected polymerisable crosslinking groups, P are independently selected spacer groups, T are independently selected end groups which are chosen from hydrogen, an alkyl chain, an alkoxy chain, a cyano group or a fluorine, or where the T group comprises an alkyl chain or an alkoxy chain, the chain is optionally terminated with terminal crosslinking groups, m are independently selected from values of from 1 to 4, n is equal to 1 to 3.

2. The OLED according to claim 1, wherein the materials display liquid crystalline order.

3. The OLED according to claim 1, wherein the materials display nematic order.

4. The OLED according to claim 1, in which x is between 0 and 4.

5. The OLED according to claim 1, wherein each B is independently selected from:

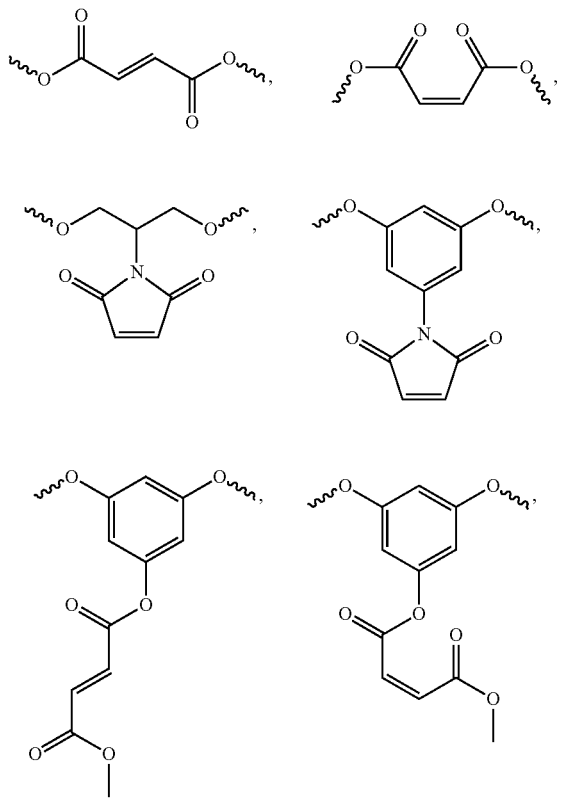

-continued
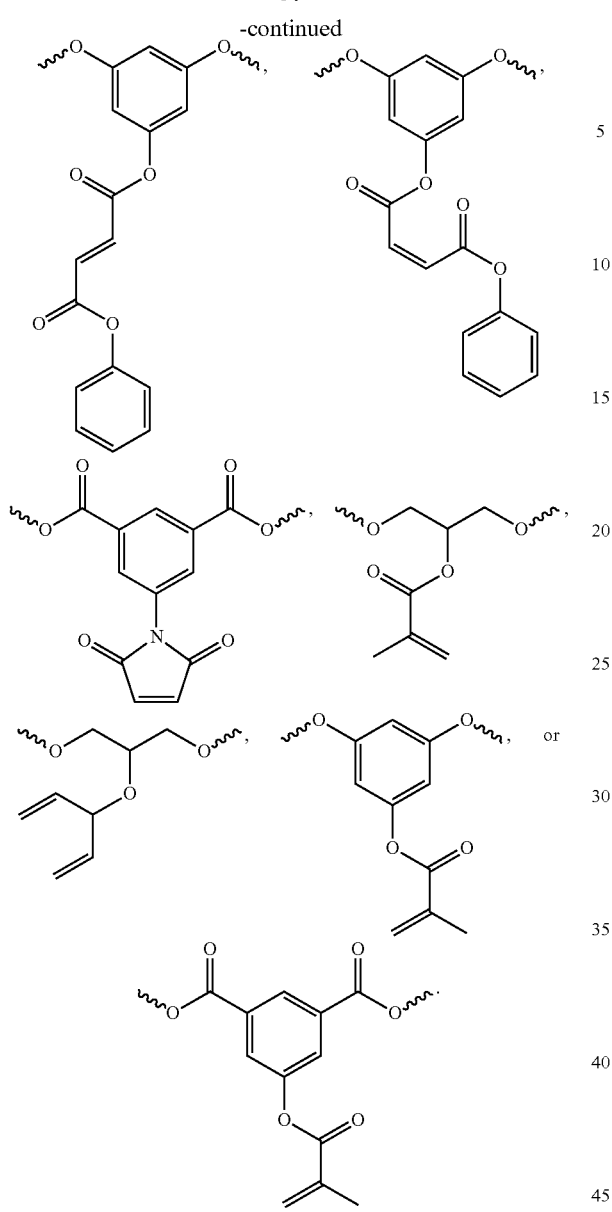
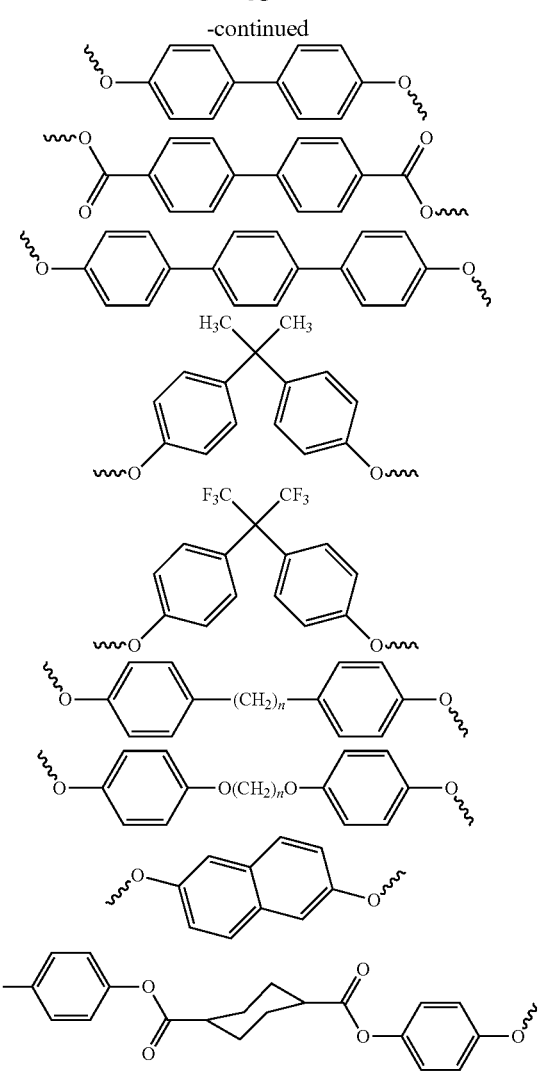
6. The OLD according to claim 1, wherein each P is independently selected from:
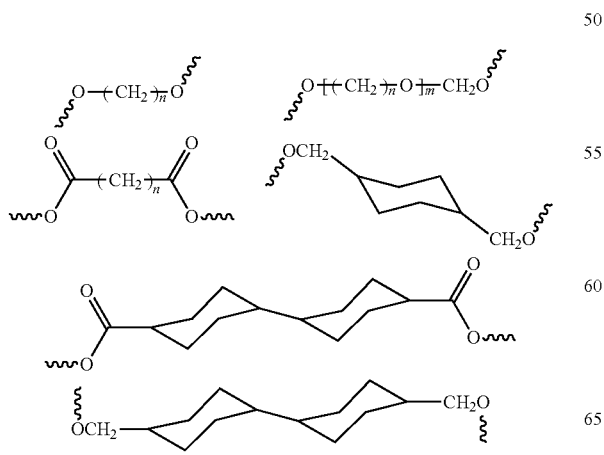
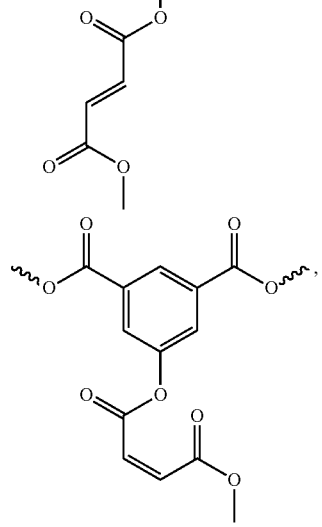

49
-continued
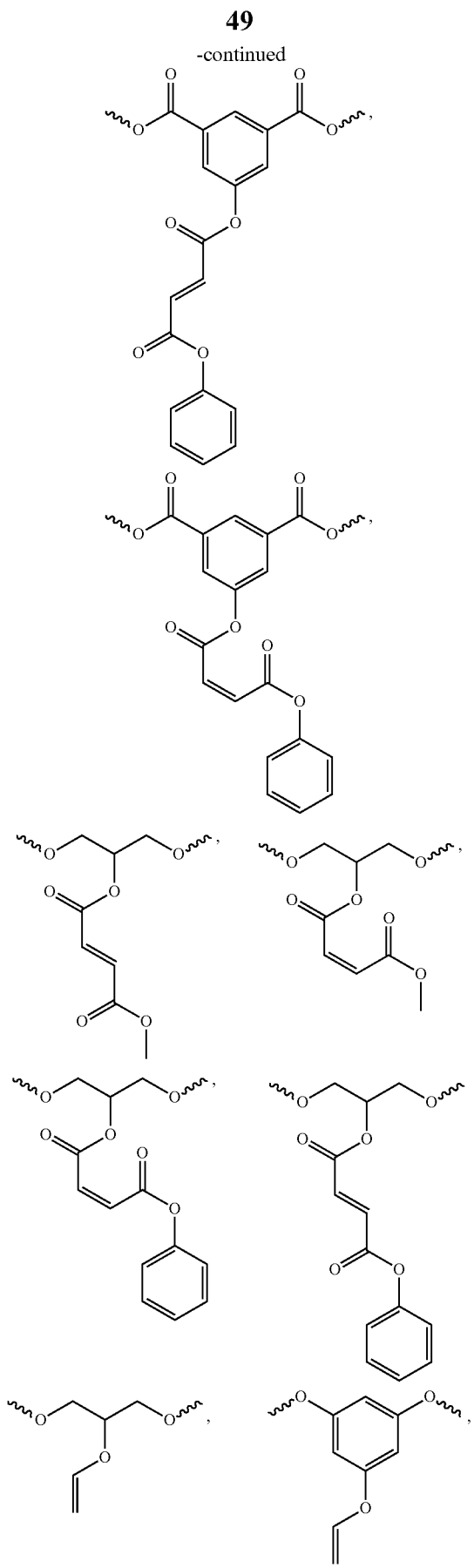
50
-continued
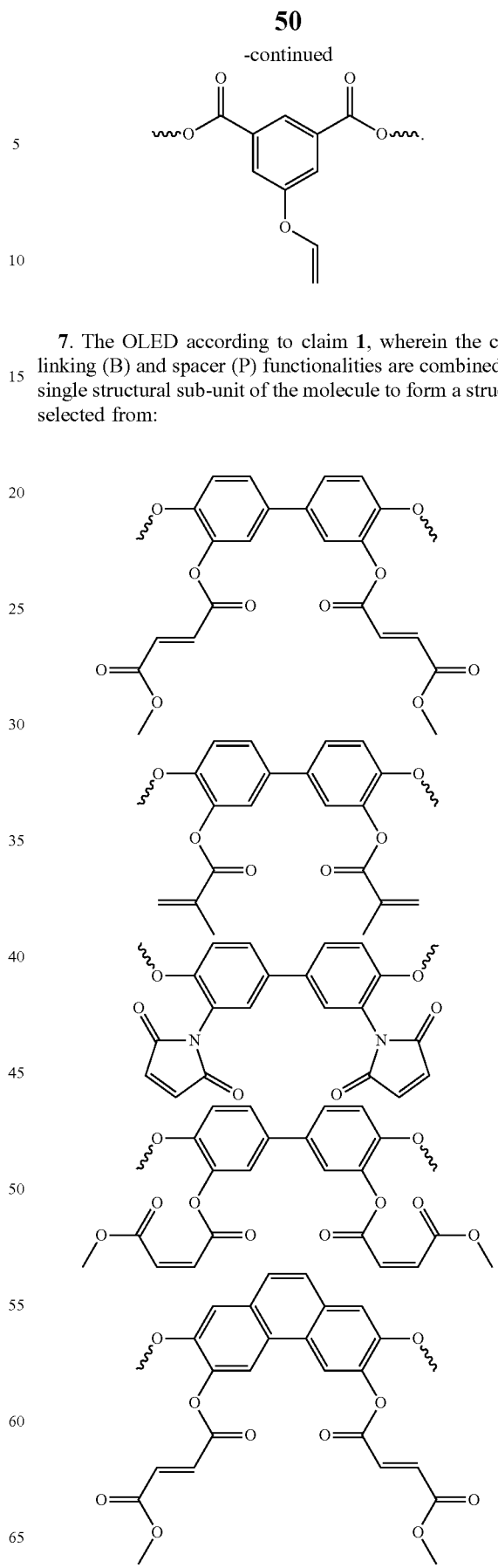
7. The OLED according to claim 1, wherein the cross-linking (B) and spacer (P) functionalities are combined in a single structural sub-unit of the molecule to form a structure selected from:

-continued
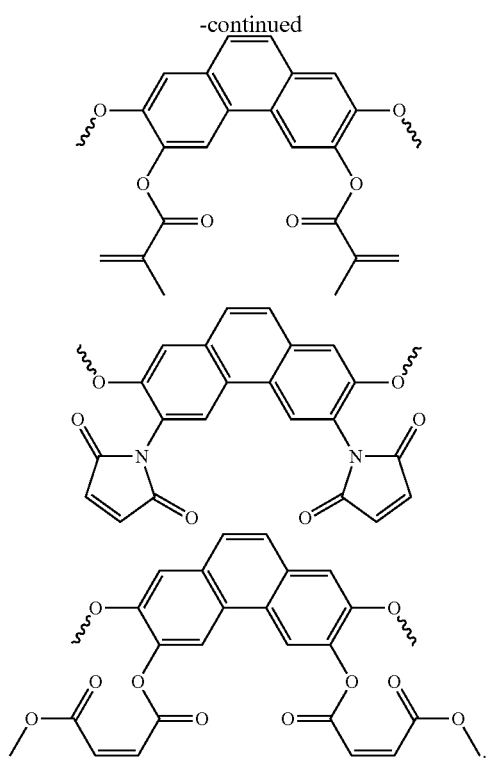
8. The OLED according to claim 1, wherein the terminal cross linking groups are selected from:
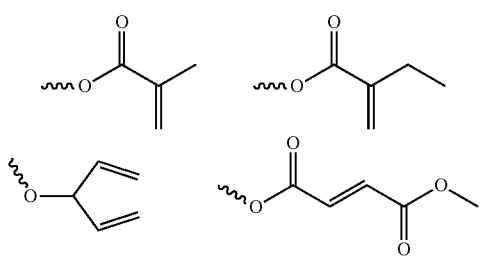
-continued
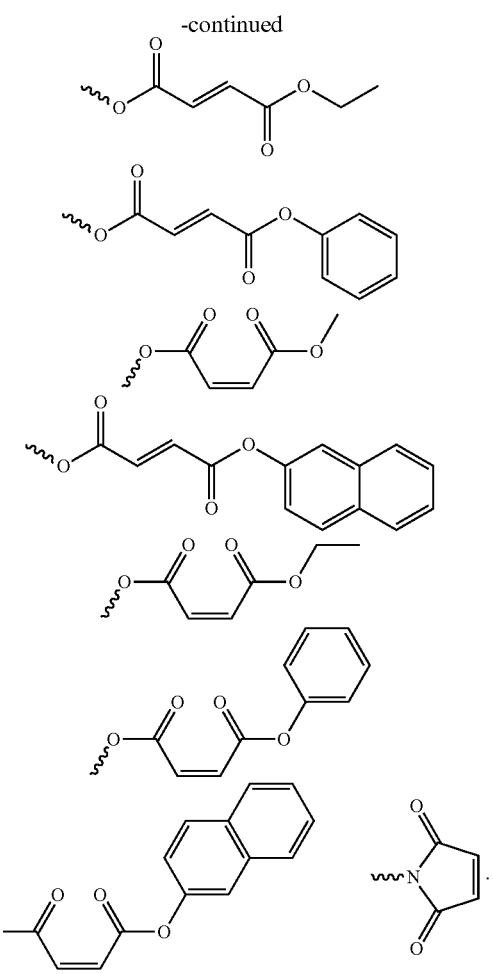
9. An OLED device comprising the OLED materials according to claim 1.
10. An OLED device formed by crosslinking the OLED materials according to claim 1 wherein the crosslinking groups are polymerized by exposure to UV light.
* * * * *